(12) United States Patent
Mahmood

(10) Patent No.: US 11,321,652 B1
(45) Date of Patent: May 3, 2022

(54) SMART LABEL DEVICES, SYSTEMS, AND METHODS

(71) Applicant: VINETI INC., San Francisco, CA (US)

(72) Inventor: Khurram Mahmood, San Ramon, CA (US)

(73) Assignee: VINETI INC., San Francisco, CA (US)

( * ) Notice: Subject to any disclaimer, the term of this patent is extended or adjusted under 35 U.S.C. 154(b) by 240 days.

(21) Appl. No.: 16/729,410

(22) Filed: Dec. 29, 2019

Related U.S. Application Data

(63) Continuation-in-part of application No. 16/698,553, filed on Nov. 27, 2019.

(60) Provisional application No. 62/807,751, filed on Feb. 20, 2019.

(51) Int. Cl.
  *G06Q 10/06* (2012.01)
  *G06Q 50/28* (2012.01)
  *G16H 20/10* (2018.01)
  *G06N 20/00* (2019.01)

(52) U.S. Cl.
  CPC ....... *G06Q 10/06316* (2013.01); *G06N 20/00* (2019.01); *G06Q 50/28* (2013.01); *G16H 20/10* (2018.01)

(58) Field of Classification Search
  CPC .. G06Q 10/06316; G06Q 50/28; G06N 20/00; G16H 20/10
  See application file for complete search history.

(56) References Cited

U.S. PATENT DOCUMENTS

| | | |
|---|---|---|
| 7,774,243 B1 | 8/2010 | Antony et al. |
| 10,244,965 B1 | 4/2019 | Gibson |
| 10,817,949 B1 | 10/2020 | Wieduwilt et al. |
| 2002/0187526 A1 | 12/2002 | Ruben et al. |
| 2006/0172422 A1 | 8/2006 | Dzekunov et al. |
| 2014/0136259 A1 | 5/2014 | Kinsey, II et al. |
| 2017/0039330 A1 | 2/2017 | Tanner, Jr. et al. |
| 2017/0364637 A1 | 12/2017 | Kshepakaran et al. |
| 2018/0096175 A1 | 4/2018 | Schmeling et al. |
| 2018/0096347 A1* | 4/2018 | Goeringer .......... G06Q 10/0832 |

(Continued)

FOREIGN PATENT DOCUMENTS

| | | |
|---|---|---|
| WO | 2001024771 A1 | 4/2001 |
| WO | 2012099973 A2 | 7/2012 |

(Continued)

OTHER PUBLICATIONS

Levine et al., "Global Manufacturing of CAR T Cell Therapy," Molecular Therapy: Methods & Clinical Development vol. 4 Mar. 2017, pp. 92-101.

(Continued)

*Primary Examiner* — Mahfuzur Rahman
(74) *Attorney, Agent, or Firm* — Perkins Coie LLP

(57) ABSTRACT

The subject disclosure relates to systems, methods, and devices corresponding to smart label devices. Furthermore, disclosed are smart label systems that include individualized medicine modules communicatively coupled with smart label devices. Furthermore, a method is disclosed that comprises receiving, by the smart label control system, detection data from the smart label device, wherein the detection data represents a geo-locational boundary signal. The method further comprises disabling, by the smart label control system, a rendering of content on a display of the smart label device.

18 Claims, 13 Drawing Sheets

(56) References Cited

U.S. PATENT DOCUMENTS

| | | | |
|---|---|---|---|
| 2018/0264347 A1 | 9/2018 | Tran et al. | |
| 2018/0336554 A1* | 11/2018 | Trotter | G06Q 20/3823 |
| 2019/0012666 A1* | 1/2019 | Krauss | H04L 9/3236 |
| 2019/0088373 A1 | 3/2019 | Sarmentero | |
| 2019/0096534 A1 | 3/2019 | Joao | |
| 2019/0214116 A1* | 7/2019 | Eberting | G16H 50/30 |
| 2019/0214119 A1 | 7/2019 | Wachira et al. | |
| 2020/0058381 A1 | 2/2020 | Patel | |
| 2020/0167725 A1 | 5/2020 | Bolene et al. | |
| 2020/0179230 A1* | 6/2020 | Molloy | G16H 20/13 |
| 2020/0258605 A1* | 8/2020 | Blechman | G16H 40/67 |
| 2020/0364588 A1 | 11/2020 | Knox | |
| 2021/0110897 A1 | 4/2021 | Ginsburg et al. | |
| 2021/0280287 A1 | 9/2021 | Mahmood et al. | |

FOREIGN PATENT DOCUMENTS

| | | |
|---|---|---|
| WO | 2015142675 A2 | 9/2015 |
| WO | 2017079703 A1 | 5/2017 |
| WO | 2017096327 A2 | 6/2017 |
| WO | 2017117112 A1 | 7/2017 |
| WO | 2018187332 A1 | 10/2018 |
| WO | 2019055896 A1 | 3/2019 |

OTHER PUBLICATIONS

Olweus J. (2017). Manufacture of CAR-T cells in the body. Nature biotechnology, 35(6), pp. 520-521. https://doi.org/10.1038/nbt.3898.

Merhavi-Shoham et al., "Adoptive Cell Therapy for Metastatic Melanoma," The Cancer Journal, vol. 23, No. Jan./Feb. 2017, pp. 48-53.

Kochenderfer et al., "Lymphoma Remissions Caused by Anti-CD19 Chimeric Antigen Receptor T Cells Are Associated With High Serum Interleukin-15 Levels," J Clin Oncol. Jun. 1, 2017,35(16):1803-1813. doi: 10.1200/JCO.2016.71.3024. Epub Mar. 14, 2017. PMID: 28291388; PMCID: PMC5455597.

Vineti Inc., Product Data Sheet, www.vineti.com, 2021, 2 pages.

Vineti, Inc., "Cell and Gene Therapy, Supply Chain Management: Readiness Checklist," 2021, 4 pages.

Vineti, Inc., "Chain of Identify (COI) Identifier, An industry standard recommendation for personalized therapeutics, As presented to the Standards Coordinating Body for Regenerative Medicine," Oct. 2020, 15 pages.

Vineti, Inc., "Personalized Supply Chain Strategies, A Supply Chain Readiness Guide for cell therapies, gene therapies, and personalized cancer vaccines," 2020, 22 pages.

PCT/US2019/63747—International Search Report dated Mar. 10, 2020, 2 pages.

* cited by examiner

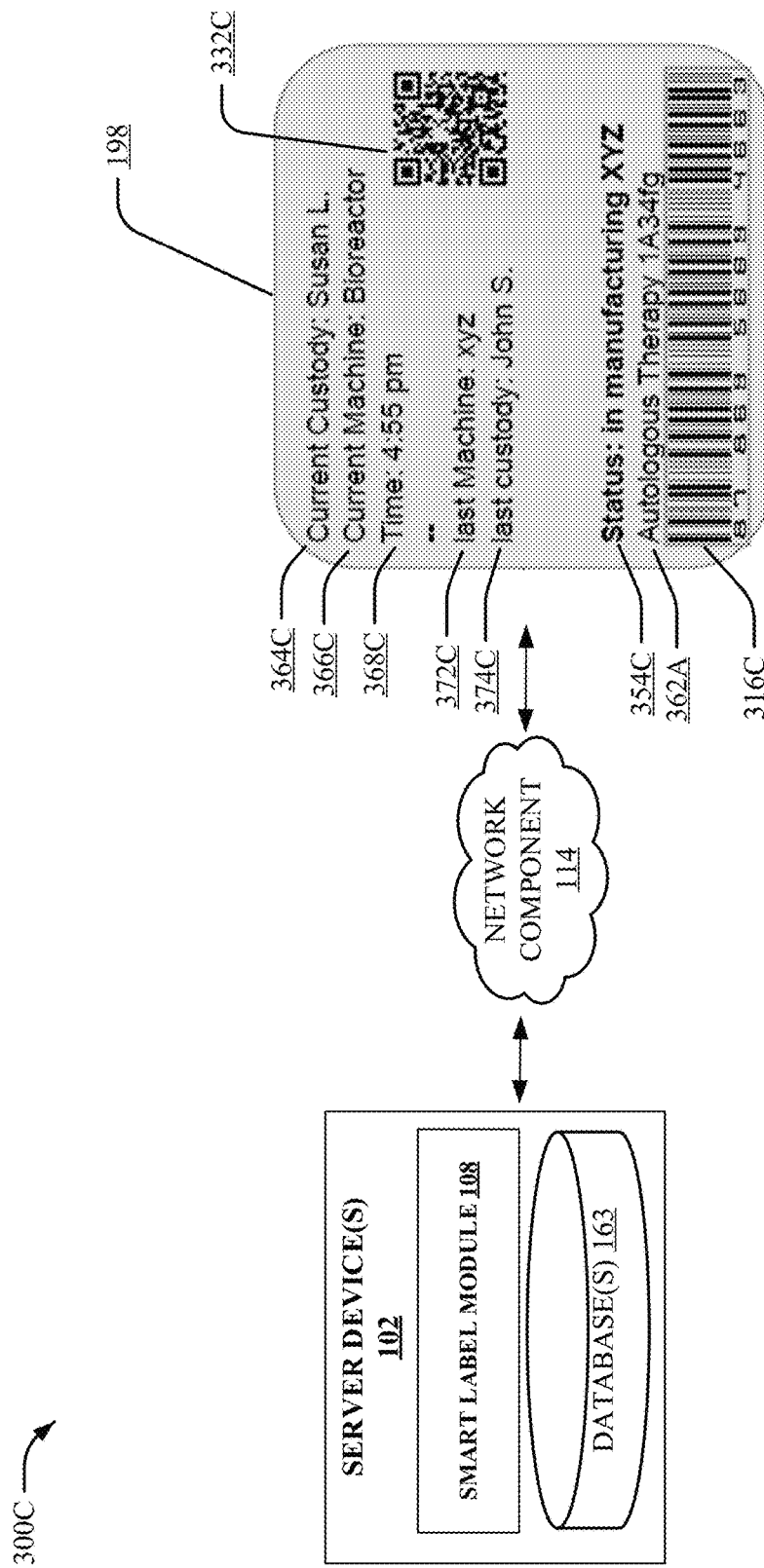

SMART LABEL DEVICES, SYSTEMS, AND METHODS

CROSS-REFERENCE TO RELATED APPLICATIONS

This application claims priority to U.S. Provisional Patent Application No. 62/807,751 titled, "Smart Label Devices, Systems, and Methods", filed Feb. 20, 2019 and U.S. Non-Provisional patent application Ser. No. 16/698,553 titled, "Centralized and Decentralized Individualized Medicine Platform", filed on Nov. 27, 2019, which claims priority to U.S. Provisional Patent Application No. 62/772,955 titled, "Centralized and Decentralized Individualized Medicine Platform", filed on Nov. 29, 2018. The entirety of the disclosures of the aforementioned applications are considered part of, and is incorporated by reference in, the disclosure of this application.

BACKGROUND

The recent emergence in disease prevention and treatment known as personalized healthcare offers several benefits to patients. This approach to healthcare allows for the provisioning of customized therapies to patients based on molecular disease diagnosis, genetics, and calculated predictions of which treatments may work best for a particular patient. For instance, CAR-T cell therapy is a cancer treatment that involves the extraction of T-cells from a patient and modifying the cell genetics to express chimeric antigen receptors that facilitate the tumor cell death. Although, these personalized treatments are revolutionizing disease treatment, a complex chain of processes must be undertaken in order to produce the therapeutics ultimately administered to the patient.

Often the process begins with the extraction of a patient cells or tissue which are sometimes transported to other facilities for further processing or storage before arriving at a manufacturing facility that will manufacture the therapeutic product (e.g., manufactured CAR-T cells). Once the patient-tailored therapeutic is manufactured, the product is transported from a manufacturing facility to an infusion site that will administer the therapeutic product to the patient. This generalized overview of various points along a personalized medicine supply chain can be fraught with logistical challenges, scheduling challenges, stakeholder coordination challenges, monitoring and tracking challenges, and other related problems.

For instance, there are several chain of identity and chain of custody complexities along the supply chain. This is due to the involvement of several stakeholders including medical personnel, patients, healthcare providers, centers of excellence, administrative staff (e.g., hospital or laboratories), inventory storage facilities, manufacturing facilities, couriers, and other such stakeholders will take custody of a component of a therapeutic or the therapeutic itself at some point along the supply chain. Furthermore, there are several inefficiencies that occur with respect to the shipping and delivery process of the patient material (e.g., cells, blood, etc.), the therapeutic product, and other items to be delivered along such supply chain.

As an example, to facilitate the transport of a material (e.g., patient blood) from one place to another (e.g., via a package), the material must be labeled and identified with correlated patient information. The label accompanies the material, and/or the package used to transport the material. Furthermore, as the material, intermediate product, and final product is shipped between locations (e.g., facility addresses) along the supply chain, a new label must be printed to accompany such items during shipment and for use with a destination facility. Furthermore, each facility has its own policies and quality systems that dictate what information can be included on each label. This continuous printing of labels with varying label information presents a host of problems that can disrupt the delivery of important therapeutic products, the administration of a therapeutic product, or even cause harm if administered to a wrong patient.

For instance, after apheresis collection of a patient blood at a collection center, the cells are often sent via courier to either a facility to further process the cells or directly to the manufacturing facility. As such, the label accompanying the package can include details such as the apheresis site number, chain of identity number, protected health information (PHI) of the patient, courier information, medical record number (an EMR reference), therapy specific identifier, and other such information. As the package passes through other facilities (e.g., storage, manufacturing, couriers, medical centers, etc.), a range of new labels must be prepared to accompany the package with relevant updated information (e.g., new courier, new destination, etc.) until a final regulatory approved label is affixed for receipt at the medical center or other infusion site.

Current labeling technologies and practices are fraught with challenges and susceptible to errors. In one respect, validated printers and appropriate ink (e.g. indelible ink resistant to alcohol swabs) must be used to print regulatory compliant labels at various facilities. However, the use of validated printers and ink are inefficient, take much time, resources, and labor to utilize and are vulnerable to human error, such as wrong labels being applied to patient samples or packages. Furthermore, some facilities use pre-printed labels for placement on materials or packages, however such printers may contain private patient information and are vulnerable to theft, misplacement, and privacy breaches. Also, the use of pre-printed labels requires a thorough procedural compliance for label reconciliation such as defacing and destroying unused labels. There is a need for solutions to these challenges and issues.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments, described herein are systems, devices, apparatuses, computer program products and/or computer-implemented methods that facilitate an interaction between a smart label module and a smart label device capable of accompanying an item such as a package, material, and/or biological material for shipment, use within a facility, or use by several facilities.

According to an embodiment, a computer-implemented method is provided. In an aspect, the method can include receiving, by a server device coupled to a processor, label identification data corresponding to a label identifier of a smart label device. In another aspect, the method can include verifying, by the server device, whether the label identification data is valid or invalid. In yet another aspect, the method can include assigning, by the server device, the label identification data to personal identification data representing a patient identifier.

In another embodiment, the computer-implemented method can further comprise querying, by the server device, first location data acquired from the smart label device and stored on a database of the server device or a blockchain data store, wherein the first location data represents a current location of the smart label device. Also, the method can include verifying, by the server device, that the first location data corresponds to second location data representing an authorized facility location, wherein the verifying is based on a comparison of the first location data to the second location data. In another aspect, the method can include authenticating, by the server device, that user identification data received from a user device is authorized user identification data, wherein the authenticating is based on a comparison of the user identification data to the authorized user identification data.

In yet another embodiment, the computer-implemented method can further comprise transmitting, by the server device, label update data to the smart label device based on a positive verification of the authorized facility and a positive authentication of the user identification data. Furthermore, in another embodiment, the computer-implemented method can further comprise transmitting the first location data or the user identification data to a data store, wherein the data store is a blockchain data store or the database of the server device, wherein first location data recorded at the data store represents a chain of custody event, and wherein the user identification data recorded at the data store represents a chain of identity event.

BRIEF DESCRIPTION OF THE DRAWINGS

FIG. 3C illustrates an example, non-limiting diagram of a smart label device and a change of label content data in accordance with one or more embodiments described herein.

DETAILED DESCRIPTION

Figure 1A:
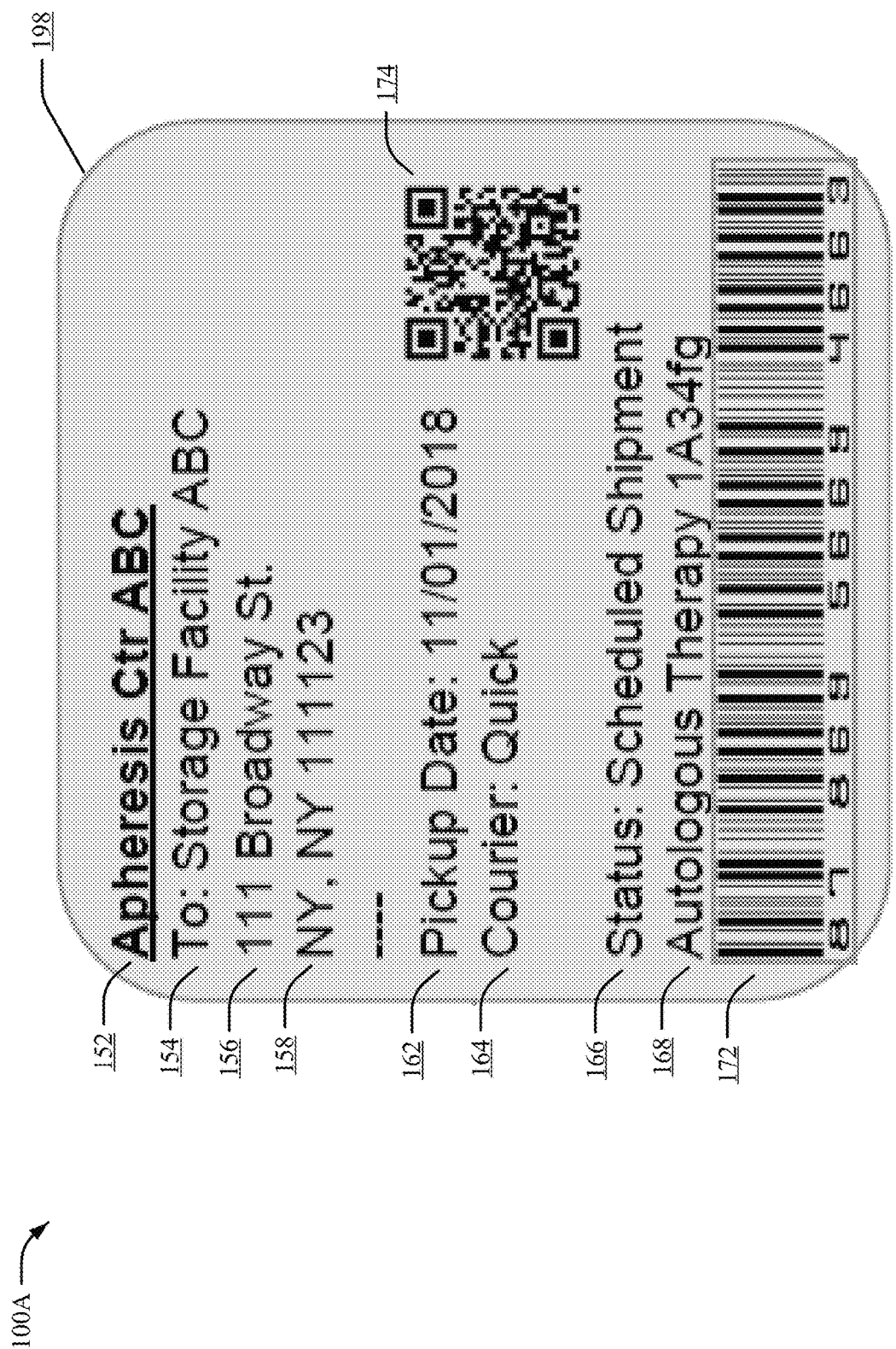
FIG. 1A illustrates an example, non-limiting diagram of a smart label device in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section. One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Disclosed herein are smart label devices and smart label systems employed by cloud-based platform technologies that allow for the controlling, configuration, and communication with one or more smart label device. Furthermore, in an aspect, the cloud-based platform technologies allow for the transmission, generation, analysis and storage of smart label data from smart label devices corresponding to package or material transportation (e.g., along a supply chain). In some embodiments, the smart label devices can also be employed as part of an individualized medicine supply chain management system. The terminology, "individualized medicine supply chain platform", "personalized medicine supply chain platform", "individualized therapeutic platform", "individualized medicine platform" or management system can denote a platform technology that facilitates the curation, analysis, processing transformation, and/or querying of data that is generated from a combination of activities, events, materials, and devices utilized by various stakeholders to procure a personalized medicine therapeutic for a patient.

In an aspect, an individualized medicine supply chain can start with a decision to treat a patient with a personalized therapy (e.g., a therapeutic medicine manufactured from a patient's own biological materials such as cells). The supply chain progresses with collecting a patient sample at a center of excellence (e.g., hospital). Thereafter, a manufacturing facility manufactures the patient-specific therapeutic medicine using the patient sample. Finally, the personalized therapeutic medicine is infused into a patient blood stream at an infusion center. A range of activities accompany this supply chain including collection of patient samples, electronic data capture of patient information, generating identification mechanisms for patient samples, sending update and confirmation notifications to stakeholders, tracking a chain of identity and a chain of custody of the patient sample and therapeutic, delivering patient samples and/or therapeutics to and from facilities, ensuring appropriate labels accompany therapeutics and samples, tracking each shipment, scheduling various tasks, and other such activities.

In an aspect, the individualized medicine platform (which can include medicine and therapeutic treatments that encompass any agent(s) or products to treat a disease such as gene therapies, cell therapies, traditional pills, antibodies, etc.) can employ various operations in accordance with coordinating and supporting the activities in a personalized medicine supply chain. Furthermore, an individualized medicine platform can employ various modules such as supply chain optimization module, commercial scale module 120-2, custody & identification module, system integrations module 140-2, and analytics module 150-2 to perform a range of operations (e.g., by providing instructions for execution by a processor of server device(s)). Amongst the range of operations that can be executed, controlled, and/or deployed by the individualized medicine platform are the safeguarding, tracking, monitoring, and identification of patient samples and patient therapeutics at all points along the personalized medicine supply chain.

In an aspect, the individualized therapeutic platform can integrate, interact with, control, configure, and communicate with smart label device(s). The individualized therapeutic platform in connection with the smart label devices can perform operations that facilitate the identification and tracking of patient samples (e.g., blood specimens) and patient therapeutics as they move along the personalized therapeutic supply chain. Furthermore, the smart label devices solve several technical problems that are pervasive with traditional labeling practices. The smart label devices disclosed herein can affix to, attach with, and/or couple with a material (e.g., patient sample, biological material, drug therapeutic specimen, blood bag) or package containing a material.

The smart label device can change, edit, update, remove, and/or add content displayed on an interface of the smart label device based on various factors (e.g., authorization credentials of current custodian, location of the material, etc.). Also disclosed herein are the systems and methods for executing and controlling operations by a smart label device, and a smart label module that can be employed by or perform operations independent of an individualized medicine platform module. For instance, the smart label module can operate as a platform to simultaneously communicate with thousands of smart label device(s) that correspond to thousands of patient materials and/or therapeutics. The smart label module can configure and control the smart label devices. For instance, the smart label module can update content that de-identifies protected health information or re-identifies protected health information based on satisfaction of rule sets (e.g., geo-fencing rules, user authentication rules, etc.) described herein.

The systems, methods and devices disclosed herein provide technical solutions to challenges associated with labeling activities corresponding to any shipment process. Traditional labels and processes for protecting label information are highly antiquated, inefficient, ineffective, and vulnerable to theft or mis-identification issues. The entire process of continuously generating new labels with new label information is tedious and vulnerable to mishaps such as mislabeling, therapeutic re-identification mishaps, and so on. An example of such issues is highlighted in relation to the development of autologous cellular gene therapy products (CGT).

A CGT product is a therapeutic derived from the cellular and sometimes directed by use of genetic material (e.g., blood) of a patient and manufactured into a patient specific therapeutic product intended for infusion into the same patient from whom it was derived. Often times the manufacturing of CGT Products begins with the collection of starting material and procedural data at a medical center (e.g., hospital, clinic, apheresis site, etc.). At this stage, a patient material must be identified as belonging to the patient and described in sufficient detail as to the constituency of the patient material. As such, a label is generated to identify the patient sample (e.g., whole blood) and other source information. For instance, the initial label for a patient sample can include apheresis site specific information, the type of cellular or genetic material collected, restrictions on the use of the material, qualifiers or disclaimers of material composition, protected health information (PHI), therapy specific information, courier specific information, manufacturer information (e.g., lot number), and/or medical record information.

This label generation process can represent the beginning of a specimen identification process which can continue at several points along the individualized medicine supply chain. For instance, the shipment of the patient material throughout the individualized medicine supply chain may include de-identifying and re-identifying label information based on authorization credentials of a custodian and/or facility policies. Furthermore, there is no provisioning for developing a chain of identity of the specimen as it travels along the supply chain. As the material begins to pass through various facilities, new labels are applied to the specimen. The new labels present information that is site and/or audience specific (e.g., specific to a cryogenic storage facility, manufacturing and distribution facility, etc.). As such, some sites are not allowed or have implemented policies that do not allow for the inclusion of certain information on material or package labels such as protected health information (PHI). The removal of such information (e.g., information that provides a reasonable basis to identify an individual) and identifiers can be referred to as de-identification and can mitigate privacy risks to individuals and support uses of data for comparative studies, policy assessments, research, and other such endeavors.

Accordingly, current labeling processes are inefficient and include some of the following mechanisms: the printing of new labels at each leg of a supply chain journey for the individualized therapeutic medicine or patient material, over-labelling where a new label is placed over an old label, or product movement which moves a product from one package or container to another package or container. The new labels can de-identify various information from the label such as PHI while within or traveling between various facilities. A de-identified label may only include, an enrollment number, a product number or other de-identified information. Once the material in its final CGT product form, it is returned to a facility for infusion into a patient. At such time, the label will again be re-identified to include the required regulatory information (e.g., PHI, quantity of therapeutic, storage requirements, manufacturing data, product care instructions) with the CGT Product. Overall, addition of labels can occur several times as a material passes from a collection site to one or more intermediate facilities, to one or more manufacturing facilities and finally to an infusion center.

This multi-faceted labeling process is unduly complex and presents multiple points of failure along a supply chain. The burden of printing new labels for each leg of a multi-legged route presents difficulty in mapping back a patient's chain of identity and maintaining a chain of custody (e.g., ensuring the data collection of who touched the product) at any given time. Also, some facilities or sponsors of a package do not allow for patient identifiers to be displayed on labels which provides a risk of improper linking of the product to an intended patient.

For instance, a de-identified product may be at risk of mis-labeling a material or providing incorrect re-identification information prior to arrival at an infusion site which can be detrimental to a patient. Furthermore, the re-identification process has other challenges such as the inability to scan a product into an electronic medical record (EMR) to positively identify a patient or having inadequate identifier information such as non-unique Investigational New Drug (IND) study numbers that are not linked to other patient identifier information such as patient identifiers in an EMR. This can lead to difficulties in identifying the material and determining to whom the material belongs.

Other issues related to label formats include the use of different label formats by several independent pharmaceutical companies. As such, most pharmaceutical companies have different label formats from one another to accompany a patient sample or therapeutic (e.g., CGT product). Furthermore, some collection sites use validated printers (e.g., pharmaceutical company approved) to print each pharmaceutical company label such that each validated printer requires its own setup, maintenance, security and connectivity for a hospital, pharmaceutical company or collection center.

Additionally, such a massively distributed printer network can be difficult to support, scale, and may require costly IT resources. Other label formats can be printed at a pharmaceutical site and shipped to a collection center or hospital. However, this process is not a scalable solution, is non-compliant with label reconciliation requirements, and can cause an incurrence of high shipping costs. The smart label devices, systems, and methods disclosed herein provide technical solutions to the challenges and issues with current labeling processes.

The smart label systems and modules disclosed herein can provide updated content to a smart label device display and receive smart label data from smart label device components (e.g., sensors, input data, modules, etc.). As such, the smart label systems can provide de-identifying information and re-identifying information to the smart label device as it moves from a first location to a second location and between a first custodian and a second custodian during specimen or package transition points including points along individualized medicine supply chain.

This technology disclosed herein also eliminates the need for printers to continuously print labels, add, and remove labels to be associated with a material or product as it travels to various facilities with different information access rights. Furthermore, the technology allows for an efficient, transparent, and constant communication mechanism between smart label devices, server devices, and data stores. These interactions can allow for a mapping of chain of custody event data, chain of identity linked data, and/or transaction data associated with the material to components of the individualized medicine platform module that employs a smart label module.

Furthermore, the disclosed technology and embodiments cut costs associated with providing validated printers and printing labels. Also, a specimen or package label can be re-identified at appropriate times with patient data, which alleviates the risks and vulnerabilities associated with potential mis-identification or non-identification of materials with traditional labeling processes. In another aspect, the smart label devices and systems can efficiently provide content updates or transmit data to the smart label device based on validation of location data and/or user authorization credentials provided to the smart label system by the smart label device via smart label data transmission.

Also, in some non-limiting implementations, security mechanisms can be employed by eliminating or reducing data storage on the smart device and instead maintaining all data store capabilities to the individualized medicine platform module, the smart label module, and/or an independent data store (e.g., blockchain). As such, the chain of identity events and chain of custody events can be recorded on an immutable ledger such that smart label module can perform custody or identity audits upon request. Thus, in an embodiment, a bad actor or custodian cannot steal data from the smart label device itself but would have to access an encrypted data store. In other non-limiting implementations, the individualized therapeutic platform and the smart label system can be separate platforms that are integrated communicatively. Furthermore, a chain of custody event recorded on an immutable distributed ledger (e.g., blockchain) can ensure that if unexpected or non-intended deviations in custody occur, an investigation of the chain of custody events can be conducted. Also, if an adverse event or recall of a particular product occurs due to post administration of a treatment then the chain of custody and/or chain of identity recordation can be utilized to conduct a full investigation of the chain of custody trail and/or chain of identity trail to ascertain any issues that may have arisen due to a custodian of the therapy (e.g., quality control staffer, regulatory staffer, etc.).

Turning now to FIG. 1A, illustrated is an example, non-limiting diagram 100A of smart label device(s) 198 in accordance with one or more embodiments described herein. In an aspect, smart label device(s) 198 can represent a device comprising a digital display capable of affixing or adhering to a package, material, specimen, sample or item (referred to as any of the foregoing throughout the disclosure). The smart label device(s) 198 can be configured to display update data (e.g., de-identified information, PHI, or other such information) or content at the display based on label requirement rule sets. As such, smart label device(s) 198 can display different content at different facilities, to different users or custodians of an item and smart label device(s) 198, or locations to which the smart label devices are located.

In a non-limiting embodiment, smart label device(s) 198 can be configured with an electronic ink (e-ink) programmable display having low power requirements to display content. Furthermore, smart label device(s) 198 can be powered by a range of battery technologies that allow power to transmit to the smart label device(s) 198 for several weeks or longer. In another non-limiting embodiment, smart label device(s) 198 can include a GSM/3G radio antenna with added remote commands. Furthermore, smart label device(s) 198 can utilize a tamper-resistant hardware to prevent tampering with the label or label information. In another non-limiting embodiment, the smart label device(s) 198 can include hardware-based cryptographic tokens to perform two-factor authentication of one or more user of smart label device(s) 198.

For instance, a user device requesting access to updated label information can transmit input data representing a personal identification number (PIN) displayed on a token identification device, to a smart label module 108 of server device(s) 198. The smart label module 108 can perform validation operations that approve of the input PIN as valid or disprove of the number as invalid. Upon validation of the PIN, the smart label module 108 can transmit updated data to smart label device 198 for rendering of such updated label information at a display (e.g., E-ink display). In other non-limiting embodiments, other authentication forms including multi-factor authentication tools can be utilized by smart label device(s) 198 to protect unauthorized information from being displayed at unauthorized times and by unauthorized viewers.

In another aspect, smart label device(s) 198 can employ any of a range of display types including an organic thin-film transistor (OTFT), E-ink display with flash memory storage, E-ink panel capable of representing images and/or two-dimensional codes, bi-stable LED display, LCD display shutter or LCD screen, TFT display for freezer use, displays that employ a RGB color model, and other such displays. In another aspect, the display of smart label device(s) 198 can render a range of content or updated content such as facility data 152 (e.g., identification of facility or user such as cryogenic storage facility, manufacturing facility, collection center, apheresis center, raw material facility, infusion site, hospital, clinic, etc.), destination data 154 (e.g., a name of a person or organization intended to receive the item), first address data 156 (e.g., street address), second address data 158 (e.g., city, state, zip code information), retrieval data 162 (e.g., date for item pickup), courier data 164 (e.g., identity of courier organization or personnel to pick-up item for transport, mode of transport, etc.), status data 166 (e.g., package or item status or standing at a particular point in time), descriptive data 168 (e.g., identifier of the item and/or title of the product as well as alphanumeric identifier), bar code data 172 (e.g., visual identification symbol configured to be read by a scanner, other line of sign technologies, etc.), and/or quick response (QR) code data 174 (e.g., code configured to store data such as character data).

In another aspect, smart label device(s) 198 can comprise any one or more sensor technology such as generic sensors, temperature sensors (e.g., temperature tracking of items during transportation), humidity sensors (e.g., monitoring preservation conditions of a sample), light intensity sensors (e.g., monitoring of light intensity exposure of the item), passive light sensors, accelerometers (e.g., latching bi-stable accelerometer, etc.), speed sensors (e.g., to detect a vehicle speed), color sensor (e.g., semiconductor based), photodiodes, ultrasonic beacons, and other such sensors. In another aspect, smart label device 198 can employ a range of sensors to detect environmental condition data (e.g., temperature, humidity, noise, etc.).

Furthermore, smart label device(s) 198 can employ activation sensors and/or actuator sensors such as movement sensors (e.g., gyroscopes, accelerometers, etc.) or pressure sensors to detect pressure or movement information associated with the item. In an aspect, smart label device(s) 198 can facilitate the detection of conditions pursuant to a set of condition rules corresponding to the contents of a package (e.g., biological materials needing to be stored at temperatures within a target temperature range, delicate specimens that must not be exposed to turbulence or target altitudes, etc.). In an aspect, smart label device(s) 198, can communicate sensor data to smart label module 108. Furthermore, smart label module 108 can determine whether the package contents are subjected to favorable or unfavorable conditions. For instance, smart label module 108 can compare temperature data, speed data, motion data, light intensity data, or vibration data to threshold data values for each respective parameter or a threshold value for a combination of parameters to determine the threat of various conditions (as detected by the sensors) to the quality of the package contents (e.g., biological material). Furthermore, smart module 108 can trigger a notification to various stakeholders based on detected sensor data.

As an example, if a courier of such package is an autonomous vehicle, the courier can trigger a deceleration in speed or determination of an alternative path to maintain a slower or steadier ride to preserve the condition of the package contents. In other non-limiting embodiments, smart label module 108 can control other devices based on detected sensor information from smart label device(s) 198. For instance, smart label module 108 can trigger adjustments to control the temperature of cryogenic storage compartments or refrigerated compartments based on a detected condition of the package contents as detected by smart label device(s) 198. In another non-limiting embodiment, smart label module 108 can control manufacturing processes associated with generating a personalized therapy based on detected conditions of package contents (e.g., half-life of biological materials), such controls include adjusting a speed of assembly, adjusting an order of manufacturing operations, suggesting additional steps to improve a quality of the therapeutic (e.g., centrifuging the material). In an aspect, smart module 108 can control such additional devices via communicative coupling to such other devices (e.g., manufacturing equipment, cryogenic storage equipment, etc.).

In a non-limiting embodiment, smart device(s) 198 can continuously detect data from respective smart label sensors. Furthermore, smart module 108 can continuously determine package content (e.g., package can refer to a box, blood bag, test tube, vile, or other containment modality used to store biological material) conditions based on an analysis of the continuous detected data (e.g., threshold comparisons and evaluation). The smart label module 108, can control and/or configure smart label device(s) 198 and other equipment (e.g., manufacturing equipment, cryogenic storage equipment) to execute an operation (e.g., increase or decrease a temperature or speed of manufacture, etc.) based on the detected data exceeding or registering below a target range. Furthermore, smart module 108 can detect geo-location coordinates to automatically trigger an adjustment of various conditions based on predicted parameter corresponding to such geo-location coordinates. Furthermore, smart module 108 can also access smart label information to display at a display interface of smart label device(s) 198 based on a prediction of geo-location coordinates to be reached at a target time. As such, smart module 108 in connection with smart label device(s) 198 can avert technical problems associated with the deterioration of quality of patient materials due to transportation, storage, and/or manufacturing processes.

Furthermore, in an aspect, smart label device(s) 198 and corresponding sensors can be utilized in a range of cases. For instance, smart label device(s) 198 sensors can be utilized in individualized medicine supply chains (e.g., tracking patient materials and packages), retail uses (e.g., labels to display and indicate information to consumers such as price fluctuations), logistics (e.g., product management tasks that receive data from the way a consumer interacts with the product and corresponding label), provide instructions related to the product to which it is affixed, perform item identification operations, and other such uses. In some non-limiting embodiments, smart label device(s) 198 can be configured with hardware that can perform smart label functions at extreme cold temperatures to withstand cryogenic preservation conditions (e.g., temperatures as low as −190 degrees Celsius). Furthermore, temperature sensors of smart label device(s) 198 can allow them to detect storage temperatures and smart label module 108 can compare such temperature data to threshold temperature data to determine whether the condition the material corresponding to smart label device(s) 198 is satisfactory or in jeopardy.

In one or more non-limiting embodiments, smart label device(s) 198 can also include one or more controller components such as a complementary metal-oxide-semiconductor (CMOS), hybrid CMOS, microcontroller, low frequency CMOS controller, e-paper driver, microcontroller, and/or other such controller component. In yet another aspect, smart label device(s) 198 can employ any of a range of communication technologies to perform communication operations with other devices (e.g., server device(s) 102, computer device(s) 104, individualized medicine platform module 106, smart label module 108, etc.). For instance, smart label device(s) 198 can comprise any of the following technological components or utilize any of the following technologies: radio-frequency identification (RFID), Ai-Net wireless protocols, Wi-Fi, Radio Force X4 (RFX4), infrared, nearfield communication (NFC), ultra-high frequency (UHF) RFID, and other communication modalities. In other non-limiting embodiments, smart label device(s) 198 can comprise any one or more of a range of battery technologies or power saving technologies including but not limited to lithium batteries, rechargeable batteries, duty-cycling power technologies, solar cell technologies, and photovoltaic cell technologies. As such, smart label device(s) 198 can include a range of structural elements and can be configured to operate in connection with a smart label module 108. In some non-limiting embodiments individualized medicine platform module 106 can employ smart label module 108. In other non-limiting embodiments, smart label module 108 can be a platform application executing on a server and communicatively couple with individualized medicine platform module 106.

Figure 1B:
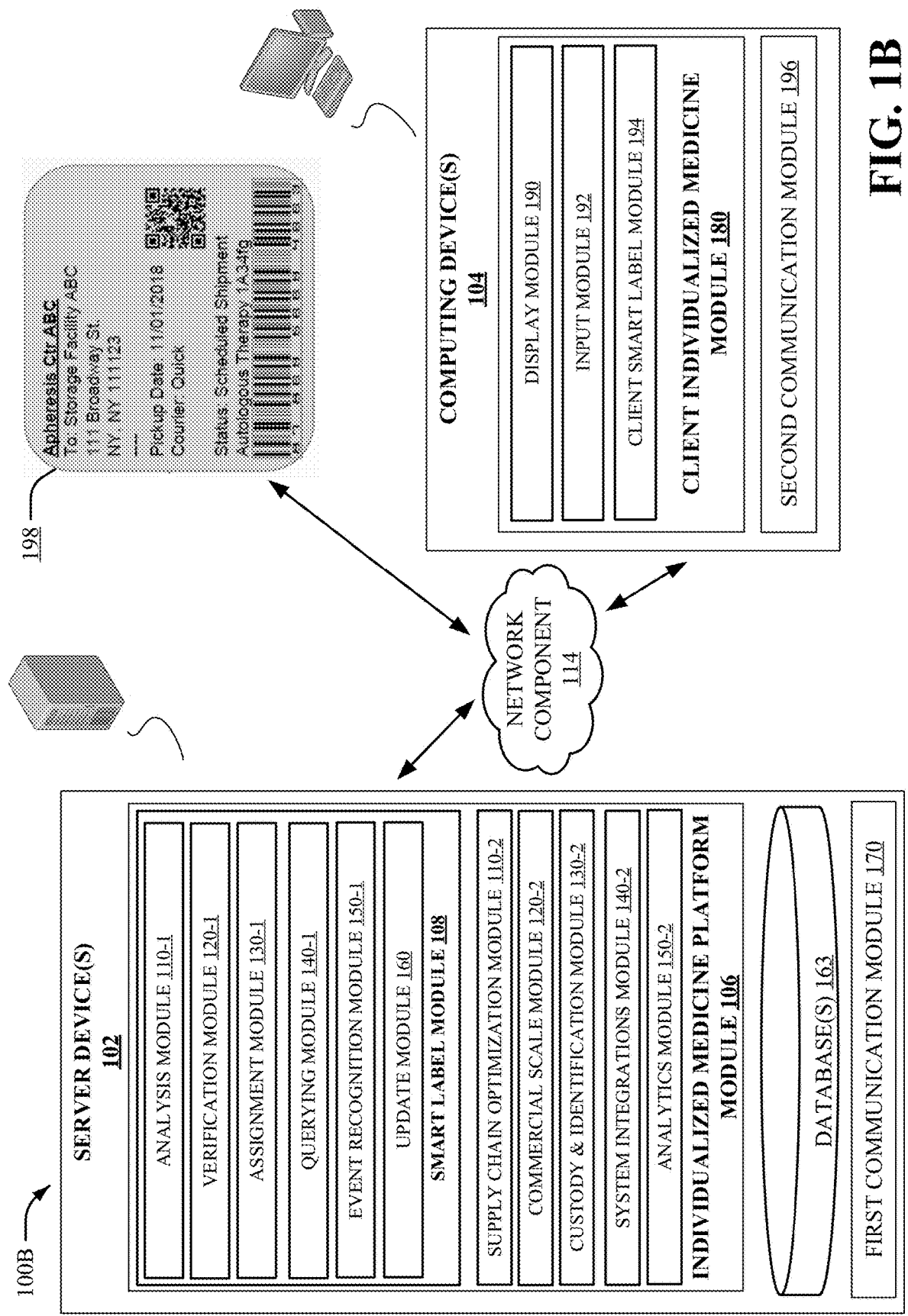
FIG. 1B illustrates an example, non-limiting block diagram of a representative environment comprising server device(s), computing device(s) and smart label devices, in which data associated with a personalized medicine supply chain platform and a smart label system can be generated, transmitted and stored in accordance with one or more embodiments described herein.

Turning now to FIG. 1B, illustrated is an example, non-limiting block diagram of a representative environment 100B comprising server device(s) 102, computing device(s) 104 and smart label device(s) 198, in which data associated with a personalized medicine supply chain platform module 106 and a smart label module 108 can be generated, transmitted and stored in accordance with one or more embodiments described herein. In a non-limiting embodiment, server device(s) 102 can comprise individualized medicine platform module 106, database(s) 163, and first communication module 170. Furthermore, individualized medicine platform module 106 can include analysis module 110-1, verification module 120-1, assignment module 130-1, querying module 140-1, event recognition module 150-1, and/or update module 160.

In another one or more non-limiting embodiment, computing device(s) 104 can include client individualized medicine module 180 and second communication module 196. In an aspect, client individualized medicine module 180 can employ display module 190, input module 192, and/or client smart label module 194. The non-limiting example environment 100B can include an example system that can be used to configure, transmit data to/from, and/or control smart label device(s) 198. Environment 100B includes server device(s) 102, computing device(s) 104, and smart label device(s) 198 that, in concert, provide smart label device(s) 198 operability, such as label content updates, label content removal, label content addition, user authentication, location-based authentication, location based identification of the smart label device(s) 198 (e.g., geo-fencing, satellite-based technologies such as global positioning satellite, triangulation, Time Difference of Arrival (TDOA), etc.), data transmission to and/or from smart label device(s) 198, and other such operations. In an aspect, computing device(s) 104 can include a device having at least one processor (e.g., digital signal processor), one or more memory, and capability of executing program applications. A computing device(s) 104 can include, but is not limited to, a smart phone, desktop computer, tablet device, personal digital assistant, set top box, and other such devices.

In a non-limiting embodiment, smart label device(s) 198 can detect one or more geo-fencing boundary and such detection (e.g., using event recognition module 150-1) can trigger transmission of event data from smart label device(s) 198 to server device(s) 102. Furthermore, in an aspect, server device(s) 102 can employ verification module 120-1 to authenticate (e.g., using security authentication parameters to access content for display at an interface of smart label device(s) 198) a location and/or custodian and/or facility associated with the detected geo-fence boundary. In an aspect, a required detection of smart label device(s) 198 of a geo-fence to trigger the display of respective content at a display of smart label device(s) 198 can provide an additional authentication and security requirement to ensure that an authorized user corresponding to valid credentials can access sensitive information at the smart label device(s) 198 interface.

Furthermore, such smart label device(s) 198 can be controlled by server device(s) 102 to only display respective sensitive information at a smart label device(s) 198 interface while such smart label device(s) 198 is located within a respective geo-locational boundary (e.g., boundary encompassing a manufacturing facility, laboratory, center of excellence, etc.). As such, server device(s) 102 in connection with geo-fencing detection can ensure that even validated users (e.g., user having authorized credentials such as login, password, etc.) cannot access sensitive information (e.g., such information is not displayed) outside of a defined facility as defined by the geo-fencing boundary. Accordingly, even if a user credentials are compromised, the geo-fencing security mechanisms of server device(s) 102 and smart label device(s) 198 to employ location awareness requirements for access of sensitive information. In yet another aspect, server device(s) 102 can correspond a detection of a geo-fence boundary with flag data to determine whether the smart label device(s) 198 is entering or exiting a geo-fenced region.

In yet another aspect, server device(s) 102 can generate a set of customized data for display at a relevant location associated with the smart label device(s) 102 location coordinates and geo-fencing authentication techniques. For instance, if a package (e.g., comprising biological material) is located at coordinates associated with a storage facility, server device(s) 102 can utilize such current location coordinates to determine the coordinates of the next facility destination for the package, which server device(s) 102 can control for display on the smart label device(s) 198. As such, a user in possession of the package (e.g., facility manager, courier, etc.) within a geo-location boundary can identify a destination location of the package by viewing the smart label device(s) 198 display. Furthermore, in an aspect, server device(s) 102 can control the triggering of alerts based on the detection of geo-location boundaries. For instance, a courier who enters a geo-locational boundary (e.g., within X miles of a facility) can be detected by smart label device(s) 198 and/or server device(s) 102 to trigger an alert to a custodian of the package to queue the package for pick-up or delivery respectively. As such, the geo-fencing implementations in connection with smart label device(s) 198 can improve wait times associated with package pick-up and drop-off and create supply chain efficiencies critical to transit of biological materials.

In one or more implementation server device(s) 102 can represent server device(s) 102 that can distribute various aspects of the smart label module 108 across multiple devices and/or provide cloud-based services to multiple user devices. Server device(s) 102 can be local to several devices, remote from the several devices, or any combination of remote and/or local to such devices. In a non-limiting implementation, server device(s) 102 can be configured as part of a cloud of one or more server computers that are connected to the multiple devices through a network, the Internet, or other data communication link. Furthermore, such cloud computing environment can communicate with any type of computerized device (e.g., smart label device(s) 198) over any type of network and/or network addressable connection. In another aspect, the cloud computing environment can include a set of functional abstraction layers such as hardware (e.g., mainframe, servers, blade servers, storage devices, etc.) and software layers (e.g., database software), virtualization layers (e.g., virtual storage, virtual networks, etc.), management layers (e.g., metering tracking, security verification, etc.), and workload layers (e.g., data analytics processing, software development, etc.). In an aspect, the workload layer can include a smart label control workload that controls and communicates with one or more smart label device(s) 198 in the manners disclosed throughout this disclosure.

In other non-limiting embodiments, server device(s) 102 can form part of an interconnection architecture such that seamless operations, and configurations can be implemented to multiple smart label device(s) 198. Furthermore, users across multiple devices can access the functionality enabled by client smart label module 194 and corresponding functionality executed by smart label module 108. For instance, thousands of users can access client smart label module 194 to request smart label module 108 (executing on server device(s) 102) to query transportation data acquired from thousands of corresponding smart label device(s) 198 in a seamless and efficient manner.

Furthermore, an individualized medicine platform module 106 can be utilized (e.g., by a central computing device such as server device(s) 102) to deploy an experience to user devices that are both tailored to each device (e.g., each computer device(s) 104 which may have different physical requirements and capabilities) and also common to all devices (access transportation data corresponding to a respective smart label device(s) 198). Furthermore, individualized medicine platform module 106 can be utilized to control and configure and control several smart label device(s) 198 in device-tailored (e.g., updating different content data on displays of each smart label device(s) 198) and common manners (e.g., configuring each smart label device(s) 198 to integrate with the respective modules employed by smart label module 108). For instance, smart label device(s) 198 can be uniquely configured (e.g., by individualized medicine platform module 106) based on courier specifications, package specifications, transport-specific qualities, and have other such varying attributes. In another aspect, individualized medicine platform module 198 can interact with any number of device classes that define its classification by physical features, types of usage, or other common characteristics of the device.

In a non-limiting embodiment, smart label module 108 can control print label operations as well such as populating label data and controlling printer administration operations (e.g., printer serial numbers) in combination with controlling smart label device(s) 198. However, smart label module 108 provides improvements to printer administration operations in that smart label module 108 does not require receipt of a ping command from a printer to control displayed label media content on a smart label device 198 display. Thus, smart label module 108 does not incur processing inefficiencies such as label printing queues associated with traditional label printing modalities. Accordingly, there is no delay or incurrence of processing cost associated with print label formatting and command pings between a print web service application and a label printer. Instead, smart label module 108 generates label formats for secure transmission to a configured smart label device(s) 198 at a faster rate than a traditional printing mechanism in that the smart label module 108 does not require the deployment of intermediate printing application services (e.g., used to protect transmission of sensitive data to a physical printer). Furthermore, smart label module 108 does not require additional security layers required by traditional printing modalities (e.g., HTTP and TLS connections) because the smart label device(s) 198 don't carry a risk of retaining patient data after a label display is changed. In some non-limiting embodiments, such patient data is only stored at a server device(s) separate from the smart label device(s) 198 (patient data is not stored locally).

The term "module" refers to any combination of hardware, software, and/or firmware that can be configured to provide the corresponding functionality such that the smart label module 108 and/or client smart label module 194 can be implemented using these hardware, software, and/or firmware combinations and such that smart label device(s) 198 can be configured, controlled and/or operated using such combinations as well. In non-limiting embodiments, server device(s) 102 can employ individualized medicine platform module 106 to perform a range of operations related to data corresponding to supply chain events related to the manufacture and administration of an individualized medicine or therapeutic. For instance, individualized medicine platform module 106 can generate, acquire, transform, curate, and analyze (e.g., using machine learning technologies) data as well as control external devices (e.g., manufacturing equipment). Furthermore, individualized medicine platform module 106 can track supply chain events, optimize resources in the supply chain, facilitate security and compliance tasks, enable an orchestration of supply chain events, facilitate ordering and scheduling activities, perform reporting tasks, facilitate system integrations, implement predictive analytics, extract machine learning insights for redeployment in altered machine learning algorithms and perform other such activities.

Furthermore, individualized medicine platform module 106 can employ various modules (not shown in FIG. 1B) such as supply chain optimization module 110-2, commercial scale module 120-2, custody & identification module 130-2, system integrations module 140-2, and analytics module 150-2 to execute and control various operations (e.g., providing instructions for execution by a processor of server device(s) 102). Furthermore, supply chain optimization module 110-2 can execute tasks that orchestrate logistical events (e.g., coordinate couriers) and perform data (e.g., representing the movement of materials and/or products through the supply chain) tracking tasks to allow for transparent visibility of activities performed along the individualized medicine supply chain. For instance, individualized medicine platform module 106 can employ supply chain optimization module 110-2 to execute scheduling operations corresponding to pickup and delivery of raw materials, final products, biological materials, and other such items by stakeholders (e.g., couriers, third party logistics providers, etc.) to create efficiencies in transportation of materials.

In some non-limiting embodiments, individualized medicine platform module 106 can also employ smart label module 108 to perform a range of operations corresponding to smart label device(s) 198 including managing and updating package level information for presentation at a display of smart label device(s) 198. For instance, smart label module 108 can dynamically and automatically update label information on a package or material including packages or materials relating to an individualized medicine therapy. In other non-limiting embodiments, smart label device(s) 198 can be an independent platform apart from individualized medicine platform module 106 but still perform inter-operability functions with individualized medicine platform module 106 in some instances.

In some non-limiting embodiments, smart label module 108 can integrate with individualized medicine platform module 106 to curate, analyze and transmit a broad mix of data and information to smart label device(s) 198 based on a set of rules being satisfied and/or requirements being fulfilled. In some instances, rules can target custodial criteria, location criteria, regulatory criteria (e.g., GAMP requirements, Health Insurance Portability and Accountability Act requirements, European Union's General Data Protection Regulation, NIST cybersecurity guidelines, etc.). For instance, smart label module 108 can determine whether to update (e.g., using update module 160) new content information for display at smart label device(s) 198 based on satisfaction or non-satisfaction of authentication access rules, geo-locational rules, facility content display rules, regulatory rules, and/or other such rules. Furthermore, by allowing such content changing capabilities, smart label module 108 in combination with smart label device(s) 198 enables a package (containing an individualized medicine therapeutic or material) to travel from facility A to facility Z via couriers B, C, and D without having to change labels between each facility or custodian (e.g., courier) possessing the package. As such, smart label module 108 can update (e.g., using update module 160) the content displayed at smart label device(s) 198 at each facility or upon transfer to each custodian of the package.

Furthermore, smart label module 108 can also acquire, extract, access, and/or curate data from smart label device(s) 198. Furthermore, smart label module 108 can utilize such data to procure insights such as predictive insights (e.g., future temperature, potential problems in the supply chain, etc.). In an aspect, smart label module 108 in connection with one or more processor of server device(s) 102 can execute a range of operations. For instance, smart label module 108 can support multiple computing device(s) 104, each of which is associated with a respective user, customer, organization, employee, patient, stakeholder (e.g., couriers, manufacturers, case managers, providers, hospitals, collection centers, clinics, storage facilities, etc.), and/or other users. Accordingly, each user profile can perform various operations related to smart label device(s) 198.

For instance, a patient can access via a user profile of the client individualized medicine module 180 and input requests (e.g., using input module 192) related to smart label device(s) 198 via client smart label module 194. As such, a smart label module 108 can execute queries (e.g., using querying module 140-1) based on the request and acquire data related to the query. Furthermore, analysis module 110-1 can employ analytics operations to procure insights from the queried and acquired data for display at display module 190 of computing device(s) 104. For example, a user device may request identity data corresponding to the custodian of a specimen, the location of the specimen, and the content displayed on the smart label device(s) 198 at a given time. Accordingly, querying module 140-1 can access smart label device(s) 198 to acquire some of the respective data and/or in some embodiments access a data store (e.g., database(s) 163) that stores all such acquired data in response to the request. Furthermore, analysis module 110-1 can perform insight extraction operations on the acquired data to procure insights.

As such, smart label module 108 can perform a range of operations including transmitting data to computing device(s) 104 and smart label device(s) 198 (e.g., updated content data). Also, smart label module 108 can receive data and/or instructions (e.g., data query requests, content update requests, rule sets, etc.) from smart label device(s) 198 and/or computing device(s) 104. In another aspect, smart label module 108 can perform remote management operations on the smart label device(s) 198, such as associate or remove an association, delete a relationship or update a relationship of/between the smart label device(s) and a material or package. In another aspect, smart label device 198 can be controlled via smart label module 108, which can also manage data that is extracted from the smart label device 198. In another aspect, smart label module 108 can manage and process the data collected from smart label device(s) 198; provide appropriate data and content to the smart label device(s) at the correct time based on satisfaction of validation and authentication requirements; and access relevant data and events gathered and generated by the smart label device(s) 198 and stored in a data store or blockchain.

Furthermore, in an aspect, smart label device(s) 198 can be re-utilized and reconfigured for use with other packages after completing a journey with a target package. Unlike traditional labels that must be printed and disposed of as well as replaced with new labels during each leg of a journey, smart label module 108 can update, add, or remove content to/from a display of smart label device(s) 198 such that the smart label device(s) 198 itself need not be changed, merely the content for display updated. In other aspects, smart label module 108 can authenticate custodians of smart label device(s) 198 and collect requests to update label data (e.g., display updated label content at smart label device(s) 198) based on the position of smart label device(s) 198 or upon receiving a command from smart label device(s) 198 (e.g., based on an actuation mechanism).

In yet another aspect, smart label module 108 can implement predictive analytic techniques based on data acquired from the smart label device(s) 198. For instance, smart label module 108 may generate and trigger transmission of an alert (e.g., to a stakeholder device such as a courier device, autonomous vehicle, cryogenic storage facility, manufacturing equipment, etc.) if package conditions, biological material conditions or environmental conditions are determined to be beyond a target threshold for such conditions (e.g., above a target temperature). In another aspect, smart label module 108 can generate a notification based on navigational consistencies or inconsistencies of smart label device(s) 198. For instance, smart label module 108 can generate notifications based on delayed package deliveries, change of routes, scheduling changes, facility changes (e.g., manufacturer malfunctions, etc.), and other such navigational factors.

Furthermore, in an aspect, smart label device(s) 198 can integrate with manufacturing systems and/or employ geolocational techniques to trigger a display (e.g., using server device(s) 102) of manufacturing tasks, operations, and/or steps accomplished. For instance, as a biological material transitions from a first manufacturing step to a second manufacturing step, the smart label device(s) 198 can detect such changes and trigger the display of such manufacturing content to the smart label device(s) 198 display. As such, smart label device(s) 198 can be triggered to present content pertinent to various processes (e.g., manufacturing, storage, etc.) in connection with developing and transporting biological materials. In another aspect, smart label module 108 can receive, interpret, evaluate, and integrate data from smart label device(s) 198 and associated software, firmware, and/or hardware (e.g., sensor mechanisms) to make determinations and/or perform operations. In another aspect, smart label module 108 can manage energy conservation and/or expenditure operations of smart label device(s) 198. For instance, smart label module 108 can control sleep activities and/or waking activities of smart label device(s) 198 as well as enable and/or disable respective smart label device(s) 198 functions to manage energy usage.

In other non-limiting embodiments, smart label module 108 can interact with modules (not illustrated) employed by individualized medicine platform module 106 such as supply chain optimization module, commercial scale module 120-2, custody and identification module, and system integrations module 140-2. For instance, supply chain optimization module can generate instructions to order raw materials, patient samples, intermediary materials, final products, and other items for purposes of developing an individualized therapeutic product. In an aspect, smart label module 108 can acquire and curate location data, shipping status data, and other such data from smart label device(s) 198. Furthermore, such smart label data can be coupled with order data generated by supply chain optimization module of individualized medicine platform module 106 to verify that an order has been executed, confirm a status of an order, compare custodian data associated with an order to smart label custodial data indicating an identify of a custodian of a package at any given time, and other such operations.

In another aspect, supply chain optimization module 110-2 of individualized medicine platform module 106 can generate or receive scheduling data that can represent activities associated with developing an individualized therapy product such as delivery of a kit, collection of blood, shipment status of a raw material and other such activities. Furthermore, in an aspect, individualized medicine platform module 106 can utilize data acquired by smart label module 108 and generated by smart label device(s) 198 to confirm the occurrence or non-occurrence of scheduled activities (represented by scheduling data received by supply chain optimization module). As such, smart label module 108 can acquire location data, shipment status data, custodian identity data, facility data and other such data from smart label device(s) 198, where such smart label data can be matched to scheduling data to contribute to the verification of the occurrence or non-occurrence of a scheduled activity.

In yet another aspect, supply chain optimization module 110-2 can execute product and/or material tracking operations. As such, smart label module 108 can acquire data generated by smart label device(s) 198 and transmit such data to supply chain optimization module to support material tracking operations. For instance, smart label module 108 can acquire location data of several packages or materials throughout a supply chain. In some instances, several packages can be utilized for development of a single therapy such as a raw material, patient sample, intermediate material, and/or equipment item and each package can be affixed to a smart label device(s) 198. As such, smart label module 108 can acquire location data and other such data in real-time from such smart label device(s) 198 and in connection with supply chain optimization module 110-2, product tracking operations (e.g., tracking materials through a material workflow) can be performed. In another aspect, smart label module 108 can present any range of data acquired, curated, collected, generated, or analyzed by individualized medicine platform module 106 at one or more displays of smart label device(s) 198.

In another non-limiting embodiment, commercial scale module 120-2 can be employed by individualized medicine platform module 106 to perform chain of custody event verification activities. As such, commercial scale module 120-2 can acquire, curate transform, monitor, and/or store chain of identity information and chain of custody information. In an aspect, commercial scale module 120-2 can receive data sets from smart label module 108 to verify or confirm chain of identity or chain of custody events. For instance, smart label module 108 can acquire facility identification data, package custodian identification data, location data, and other such data from smart label device(s) 198 or database(s) 163 in connection with data acquired or generated by commercial scale module 120-2 to determine, confirm, identify and/or verify a chain of identity or chain of custody event. In another non-limiting embodiment, individualized medicine platform module 106 can employ custody & identification module 130-2 to generate audit trails related to handling events of materials (e.g., patient samples, products) and/or packages. In an aspect, smart label module 108 can acquire custodian data, location data, and other such data from smart label(s) 198 to support the audit trail generation operations of custody & identification module. The interactive examples between individualized medicine platform module 106, smart label module 108 and various supply chain operations related to developing an individualized therapy product are non-exhaustive.

In an embodiment, smart label module 108 either independent of or in connection with individualized medicine platform module 106 can operate as a platform that provides abstract levels of operability to one or several smart label device(s) 198 to work in concert to provide smart label controls, data acquisition, and content updates (e.g., to smart label device displays). In an aspect, smart label module 108 can employ combinations of modules (e.g., analysis module 110-1, verification module 120-1, assignment module 130-1, querying module 140-1, event recognition module 150-1, update module 160, etc.) to communicate with one another to exchange information or execute (e.g., using one or more processor of server device(s) 102) a range of operations. Furthermore, one or more rule sets can be employed to allow smart label module 108 the ability to communicate with individual smart label device(s) 198 as well as across several smart label device(s) 198.

In some respects, smart label module 108 can exchange information with smart label device(s) 198 based on rule sets that define data structures to allow cross-entity data sharing (e.g., data sharing amongst smart label device(s) 198 via smart label module 108). Furthermore, smart label module 108 can utilize rule sets to execute predictable and repeatable processing by different entities to achieve expected results related to the smart label device(s) 198. In an aspect, a data structure can include any one or more structural types that allow data to be stored, retrieved, and/or defined. As such, a data structure can include trees, queues, stacks, arrays, strings, containers, lists, graphs, bitmaps, heap objects, linked-lists, matrices, function parameters, files, and other such structures.

In yet another aspect, smart label module 108 can utilize rules to determine a prioritization of tasks such as manipulating smart label device(s) 198 based on a target operation (e.g., content update), acquiring data from smart label device(s) based on a target operation, curating data from smart label device(s) in accordance with target data storage objectives and target operation objectives. Furthermore, smart label module 108 can utilize rules such as condition-based rules, validation-based rules, mapping rules, and other such rules that can translate data structures to different data structures. In yet another aspect, smart label module 108 can provide a level of abstraction to smart label device(s) 198 that apply learned information from various sources (e.g., database(s) 163 of server device(s) 198 and/or smart label device(s) 198 components) to other sources (e.g., other database(s) or other smart label device(s) 198 by using machine learning hyper-parameter extraction techniques.

In a non-limiting embodiment, one or more processor of server device(s) 102 can execute smart label module 108 in connection with analysis module 110-1 to acquires data from smart label device(s) 198 such as sensor data, custodian data, geo-location data, authentication data, scheduling data, real-time transportation data, bar-code data (or other identification data), QR code data, or other such data. In an aspect, computing device(s) 104 can employ client smart label module 194, in combination with or independent of client individualized medicine module 180, to access analysis module 110-1, verification module 120-1, assignment module 130-1, querying module 140-1, event recognition module 150-1, and update module 160 of smart label module 108. In non-limiting embodiments, smart label module 108 can operate in combination with or independent of individualized medicine platform module 106.

In another aspect, analysis component 110 can define and/or employ entity-relationship models that identify a relationship between data sets, devices, events, objects, and/or concepts. For instance, analysis module 110-1 can specify relationships, associations, and/or dependencies between smart label device(s) 198 and physical objects (e.g., blood sample, individualized medicine therapy, package, etc.), users (e.g., courier, nurse, patient, authorized user, etc.), events (e.g., manufacture, transport, storage, infusion, geo-locational trigger event, access request event, etc.), location (e.g., facility, hospital, clinic, vehicle, etc.), a concept (e.g., a transaction, order, etc.), and so forth. As such, the relationship models can be used to define structures for storing data in a corresponding database(s) 163 (e.g., curated relational database(s) 163), define events to trigger execution of operations (e.g., trigger a content update or change of content on a smart label device 198(*s*) display), cause smart label device(s) 198 to perform a range of operations, and/or cause smart label module 108 to perform a range of operations.

For instance, in an aspect, analysis component 110 can define relationships between geo-locational data and content update operations. Furthermore, analysis component 110 can employ a rule set that causes the processor to execute a content update to a display of smart label device(s) 198 upon an acquisition (e.g., by analysis component 110) of geo-locational data that indicates the such smart label device(s) 198 is located at a target set of coordinates (e.g., within a manufacturing facility, cryogenic storage facility, hospital, clinic, etc.). Furthermore, in a non-limiting embodiment, analysis component 110 can employ another rule set that requires the processor (e.g., of smart label device(s) 198) to execute a content update to a display of smart label device(s) 198 upon an acquisition (e.g., by analysis component 110) of defined geo-locational data (from smart label device(s) 198) and upon verified receipt of authorized user or custodian credentials. Thus, analysis component 110 can define relationships, acquire data, perform analytical tasks, and/or drive various operations for performance by smart label module 108 in connection with smart label device(s) 198.

Furthermore, analysis component 110 in connection with individualized medicine platform module 106 can perform various operations as well. For instance, analysis component 110 in connection with a scheduling component of individualized medicine platform module 106 can acquire data from smart label device(s) 198 and scheduling data from a database(s) 163. Furthermore, such data can be analyzed (e.g., using analysis component 110) to generate delivery status information, relationships between package transport and logistics (e.g., via smart label device(s) 198) operations and scheduling efficiencies or inefficiencies within the individualized medicine supply chain (or other such supply chain).

In another aspect, server device(s) 102 can employ smart label module 108 in connection with verification module 120-1 to execute verification, authentication, permissions, and execute other such verification operations (e.g., in accordance with validation-based rules). In an instance, verification module 120-1 (e.g., operating on any network device such as a verification device) can be configured to verify the validity and/or authenticity of a user identity using cryptographical tokens. Furthermore, based on the validity of the authentication mechanism, such as submission of appropriate token to verify the identity of a user, analysis module 110-1 in connection with update module 160 can transmit updated content to smart label device(s) 198 for display.

In a non-limiting implementation, an authenticated user can receive a secure dynamic token cryptographically generated and configured to change with a given time interval (e.g., every few seconds). As such, at any given time a user can input the cryptographic token data (e.g., alphanumeric string) at input module 192 of computing device(s) 104. Furthermore, network component 114 can transmit the input data representing the cryptographic token data to verification module 120-1 to verify that the token data corresponds with an authorized user (e.g., via a matching mechanism, cross-referencing, etc.). In another aspect, verification module 120-1 can also verify that the smart label device is located in an authorized facility based on geo-locational fencing technology. In an aspect, a geofence can act as a virtual boundary around a target area (e.g., location, manufacturing facility, storage facility, etc.). Furthermore, smart label module 108 can utilize geolocational rules as trigger events for verification of occurrence by verification module 120-1.

For instance, verification module 120-1 can employ a positioning system comprising hardware and/or software to verify a location of smart label device(s) 198. Furthermore, analysis component 110 can acquire location data from smart label device(s) 198 and store such location data at database(s) 163. In an aspect, verification module 120-1 can verify that smart label device(s) 198 is in an authorized location or facility such that update module 160 can transmit updated content data to display(s) of smart label device(s) 198. In yet another aspect, verification module 120-1 can require the satisfaction of either a geo-locational trigger event and/or user authentication event to be satisfied in order to permit update module 160 to transmit updated label content to smart label device(s) 198.

In some non-limiting embodiments, verification module 120-1 can include a receiver, transceiver, transmitter or other such components to facilitate the receipt of location data from a positioning system or location data broadcast from smart label device(s) 198. Furthermore, verification component 120 may utilize global positioning system (GPS), GPS antenna's, Bluetooth Low Energy (BLE) beacons, Bluetooth, Wi-Fi, cellular tower triangulation or any combination of such technologies to facilitate determination of smart label device(s) 198 location. For instance, smart label device(s) 198 can transmit location coordinates (e.g., using RFID technology or GPS technologies) and/or perform geofencing activities that allow smart label module 108 to identify when the smart label device(s) 198 is located at a permittable location (e.g., authorized manufacturing facility) and trigger a transmission (e.g., using update module 160) of updated of label content. In yet another aspect, verification module 120-1 in connection with analysis module 110-1 can compare location data to geo-locational boundary data to determine whether a smart label device(s) is within an authorized area to receive updated label data (e.g., that may include Patient Health Information). In yet another non-limiting implementation, smart label module 108 can utilize an intra-location tracking system to monitor material (e.g., raw materials) movement corresponding to smart label device(s) 198 within one or more facility (e.g., hospital or manufacturing site). In one or more implementation, such intra-location tracking can be implemented using BLE.

In another aspect, smart label device(s) 198 and smart label module 108 can perform trust and authentication operations (e.g., using verification module 120-1) with one another via transmission of digital certificate security technologies. In a non-limiting implementation, a digital certificate technology in connection with hardware-based security mechanisms can restrict smart label device(s) 198 from communicating with other platforms except for individualized medicine platform module 106, smart label module 108, and/or server device(s) 102. Furthermore, in an aspect, such communication security-based mechanisms can be coupled with other secure exchange mechanisms. For instance, smart label module 106 and smart label device(s) 198 can utilize digital certificate exchange technologies or other forms of electronic security technologies that provide encryption-based security (e.g., public key, private key, keys as part of a digital certificate, etc.) for transmission of data, messages, and/or other such communications.

Furthermore, a digital certificate can be attached to service operation instruction(s) transmitted between the smart label device 198 and server device(s) 102 to allow for a verification (e.g., using verification module 120-1) process to occur (e.g., verify the identity of the smart label device 198, a location of the smart label device 198 and/or a custodian of the smart label device 198). In various non-limiting embodiments, smart label device 198 can utilize security technologies such as SSL/TLS encryption, WS-Security, Nonrepudiation, certificated-based node authentication, and/or client authentication technologies to facilitate security aspects of smart label device 198.

In any of the above scenarios, analysis module 110-1 can draw conclusions about data (e.g., location data, authentication data, sensor data, schedule data, etc.) acquired from smart label device(s) 198 by applying machine learning algorithms, data mining algorithms, and/or principal component analysis algorithms to identify data relationships between data from one or more smart label device(s). In another aspect, analysis module 110-1 can utilize machine learning algorithms to label sets of data, compare the data sets for similarities, group sets of data based on the similarities and perform similarity comparisons between the sets of data. Over time, analysis module 110-1 can iteratively analyze data, models, and relational data between data sets to improve the performance of activities such as executing scheduling activities, modes of transport, authentication techniques, and the systems overall operation (e.g., faster access to data, more accurate data extraction, faster data analysis techniques, etc.).

In another aspect, update module 160 can perform update operations to data such as updating metadata, data models, content for display at smart label device(s) 198, and other such items. Furthermore, analysis module 110-1 can identity, based on data updates, what data sets are accessed and/or utilized more as compared to other data sets, and analysis module 110-1 can prioritize the data for usage based on such priorities. Furthermore, update module 160 can utilize the prioritization information to determine how to govern updating operations for data sets, such as update module 160 updating higher priority data sets more frequently relative to other data sets, updating higher use data sets more often, and other such update governance rules.

In another aspect, server device(s) 102 can execute smart module 108 in connection with assignment module 130-1 to perform matching operations. For instance, an authorized user can scan barcode data or other identification technology information (e.g., Quick Response code, RFID identifiers, etc.) displayed on smart label device(s) 198 for storage in database(s) 163. As such, assignment module 130-1 can assign the barcode identification data to a particular smart label device(s) 198 and corresponding sample as well as patient information. As such, assignment module 130-1 can execute a linking operation that links required information to identification information and a smart label device(s) 198.

In another non-limiting embodiment, smart label module 108 in connection with querying module 140-1 can perform queries on data stored at database(s) 163. For instance, smart label module 108 in connection with querying module 140-1 can query location data, authentication data, sensor data (e.g., temperature date, etc.), and other such data stored at database(s) 163. Furthermore, querying module 140-1 can perform a query in response to input data requesting a query at input module 192 of computing device(s) 104. In an aspect, the query can identify information such as tags, keywords, identification information, and other such information. In other non-limiting embodiments, various events can trigger a query such as an occurrence of a geo-locational trigger event or receipt of authentication information. For instance, if a geolocational boundary is detected, query module 140 can request location data of a target site (e.g., manufacturing facility), such that verification module 120-1 can compare the geolocational data to location data and determine whether to trigger an update (e.g., update module 160) of content to smart label device(s) 198.

In yet another non-limiting embodiment, server device(s) 102 can execute smart label module 108 in connection with event recognition module 150-1 to track and transmit chain of custody data and chain of identity data associated with smart label device(s) 198. For instance, analysis module 110-1 can acquire user authentication data or custodian data from smart label device(s) 198 indicating a user in possession of a material, therapeutic or package. As such, event recognition module 150-1 can transmit to database(s) 163, another data store, a blockchain store or other storage element the chain of custody data. The chain of custody data can represent information relating to a user, organization, or entity that is in possession of the smart label device(s) 198 and corresponding material.

For instance, a transaction relating to a submission of user authentication data, transfer of package (e.g., indicated by smart label device label change occurs or location reached), digital record transfer occurs can be transmitted by event recognition module 150-1 to a data store. Accordingly, event recognition module 150-1 can generate a chain of custody audit trail from actions or operations or registered events that occur in connection with smart label device(s) 198. As an example, chain of custody data can represent packaging temperature ranges (e.g., acquired from smart label device 198 temperature sensors), length of time a material or package is held in custody by a respective custodian, carrier performance, weather conditions during a lag of a trip (e.g., acquired from environmental sensors from smart label device 198), and other aspects.

Accordingly, smart label module 108 and event recognition module 150-1 account for each item corresponding to smart label device(s) 198 via chain of custody tracking operations. Thus, if an item is misplaced, lost, damaged, ineffective, causes harm to a patient, or has any other issues, smart label module 108 in connection with analysis module 110-1 and querying module 140-1 can access chain of custody data from a data store and trace the chain of custody to the last known checkpoint or amongst several points along a route by which the item (and corresponding smart label device(s) 198) has traveled. In another aspect, the chain of custody data derived by smart label module 108 in connection with event recognition module 150-1 and accessed from smart label device(s) 198 can ensure on-time delivery of items and be utilized to identify whether any potential item tampering occurred.

In several aspects, event recognition module 150-1 can generate and transmit chain of custody data related to collection of specimens or patient samples, transportation of the specimens or patient samples, testing of specimens, reporting of testing results, manufacturing of specimen into therapeutic, storage of specimen for preservation, and infusion of specimen into patient. In a non-limiting implementation, event recognition module 150-1 can generate chain of custody data that includes a name or identifier of each user who accesses a specimen or package containing specimen (e.g., can be input data from user to smart label module 108 in order to view updated content at smart label device(s) 198), location data corresponding to item and associated smart label device(s) 198 at target times along the supply chain, characteristics of specimen bottles or bags, characteristics of seals or packaging of specimens, characteristics of storage environment (e.g., length of time in storage and temperature data acquired from smart label device(s) 198), time stamp information (e.g., time stamp data representing time specimen received as per smart label device(s) 198, date data, etc.), user name in possession of the item, and other such information.

In another aspect, event recognition module 150-1 can generate and transmit chain of identity data to a data store as well. In an aspect, the chain of identity data can assign (e.g., using assignment module 130-1) a unique identifying number to a smart label device(s) 198 (e.g., barcode, QR code, etc.) that links the specimen or item to the smart label device(s) 198. At any point in time the smart label device(s) 198 can be cross-checked by authorized users with other identifying information to identify the ownership of the specimen, the intended destination of the specimen, and other such identifying information. Furthermore, smart label module 108 may display de-identifying data or identifying data at the display of smart label device(s) 198 based on the user's authorization or authentication credentials and/or location authorization data of the smart label device(s) 198. In another aspect, event recognition module 150-1 can generate, receive and/or transmit identification data of custodians whom handle a material (e.g., identification data can represent an identifying number, driver's license, etc.), patient reference information (e.g., patient biometrics, patient name, etc.), and other such identification data. Furthermore, in an aspect, event recognition module 150-1 can generate and store (e.g., at database(s) 163 or another data store) chain of compliance data including qualification data, courier performance history data, shipper transportation history data, route information related to a transporter, calibration data, and other such data.

In a non-limiting implementation, event recognition module 150-1 can transmit chain of identity, chain of compliance, chain of custody, and chain of condition data to data stores such as database(s) 163. In an aspect, server device(s) 102 can comprise database(s) 163 representing any suitable source of data and/or information. Database(s) 163 can represent a data store for data generated and/or acquired by individualized medicine platform module 106. In some implementations, the acquisition (e.g., using analysis module 110-1 or querying module 140-1) of information for presentation (e.g., updated label information) at smart label device 198 can be retrieved from database(s) 163. Furthermore, such retrieval can be based on an authentication event (e.g., queries GPS coordinates and verifies in an authorized location such as the correct apheresis center; can verify that an authorized user has custody of the package/material).

In some embodiments, the smart label device(s) 198 can display detailed information about various items (e.g., contextual information about the package, charts about the package delivery thus far, points in time and locations traveled, etc.), such detailed information and data can be accessed and/or retrieved from database(s) 163. In addition or alternatively to database(s) 163, some embodiments of smart module 108 in connection with analysis module 110-1 can generate relational data models based on queried data, data received by the individualized medicine platform module 106 (supply chain data, PHI, etc.), and can store such data (e.g., queried data, individualized medicine platform data) in database(s) 163 and/or a blockchain store, according to the relational data models.

In yet another aspect, server device(s) 102 can comprise first communication module 170 that communicates with external devices. In an aspect, first communication module 170 can represent a combination of hardware, software, and/or firmware configured to facilitate the exchange of information such as sensor data, video data, location data, custody data, identity data, condition data, scheduling data, media data, audio data, text data, command data, query data, message data, smart label data, individualized medicine platform data, smart label data and other such data. In a non-limiting embodiment, first communication module 170 can include one or more protocol stacks associated with a network (e.g., network component 114) over which data can be exchanged and/or firmware can be employed to process messages used in maintaining a wireless or wired communication session and perform other such operations.

In other non-limiting embodiments, first communication module 170 can include computer networking ports, such as an Internet Message Access Protocol (IMAP), a Transmission Control Protocol (TCP) port, a User Datagram Protocol (UDP) port, a Hypertext Transfer Protocol (HTTP) port, a File Transfer Protocol (FTP) port, or other such ports. In other non-limiting embodiments, first communication module 170 can include physical communication ports, such as a serial port, an audio port, a keyboard port, a display port, a parallel port, a Universal Serial Bus (USB) port, and other such physical ports. In one or more implementations, first communication module 170 can be used by server device(s) 102 to connect with other devices such as computing device(s) 104 and/or smart label device 198 via network component 114.

In other non-limiting embodiments, environment 100B can include network component 114. In a non-limiting embodiment, network component 114 can generally represent any suitable type of communication network such as cloud computing networks that facilitate a bi-directional link between various computing devices. In an aspect, network component 114 can include more than one interconnected communication networks that comprise a plurality of interconnected elements, such as Ethernet access and wireless local area network (WLAN), a wireless telecommunication network interconnected with the Internet, a wireless (e.g., Wi-Fi) access point connected to the Internet, an Internet of Things (IoT) network (e.g., smart label device network), and other such communication networks or interconnected elements. In another non-limiting embodiment, server device(s) 102, computing device(s) 104, and smart label device(s) 198 can communicate over network component 114.

In an aspect, environment 100B also includes computing device(s) 104 referenced above. In an aspect, computing device(s) 104 can employ Client Individualized Medicine Module 180 which is a module included within computing device(s) 104 configured to access individualized medicine platform module 106 and/or smart label system 108 and/or various features provided by the smart label module 108. Client individualized medicine 180 can be a client application that renders a user interface on a display of computing device(s) 104, communicates over a network component 114 to an application executing on server device(s) 102, such as smart label module 108. Throughout this disclosure, the term "module" is used to reference any combination of software, hardware, and/or firmware that can be configured to provide functionality such that smart label module 108 and client smart label module 194 can be implemented using any of these combinations.

In another implementation, computing device(s) 104 in connection with client individualized medicine module 180 can employ display module 190, input module 192, and/or client smart label module 194. In an aspect, display module 190 can facilitate user controls of display functionality of smart label device(s) 198 (e.g., requesting content updates to smart label module 108, etc.). In another aspect, input module 192 can provide a user access into features provided by smart label module 108 such as analyzing sensor data or other data of smart label device(s) 198, accessing chain of custody and/or chain of identity data, and/or tracking a smart label device(s) 198 and other such activities. In another aspect, computing device(s) 104 can employ second communication module 196 configured to communicate with server device(s) 102 and respective modules employed by server device(s) 102 (e.g., smart label module 108). Furthermore, second communication module 196 can represent any suitable combination of hardware, software, and/or firmware configurable to facilitate data exchanges, instruction exchanges, rule exchanges, and other communication exchanges with other devices.

Figure 1C:
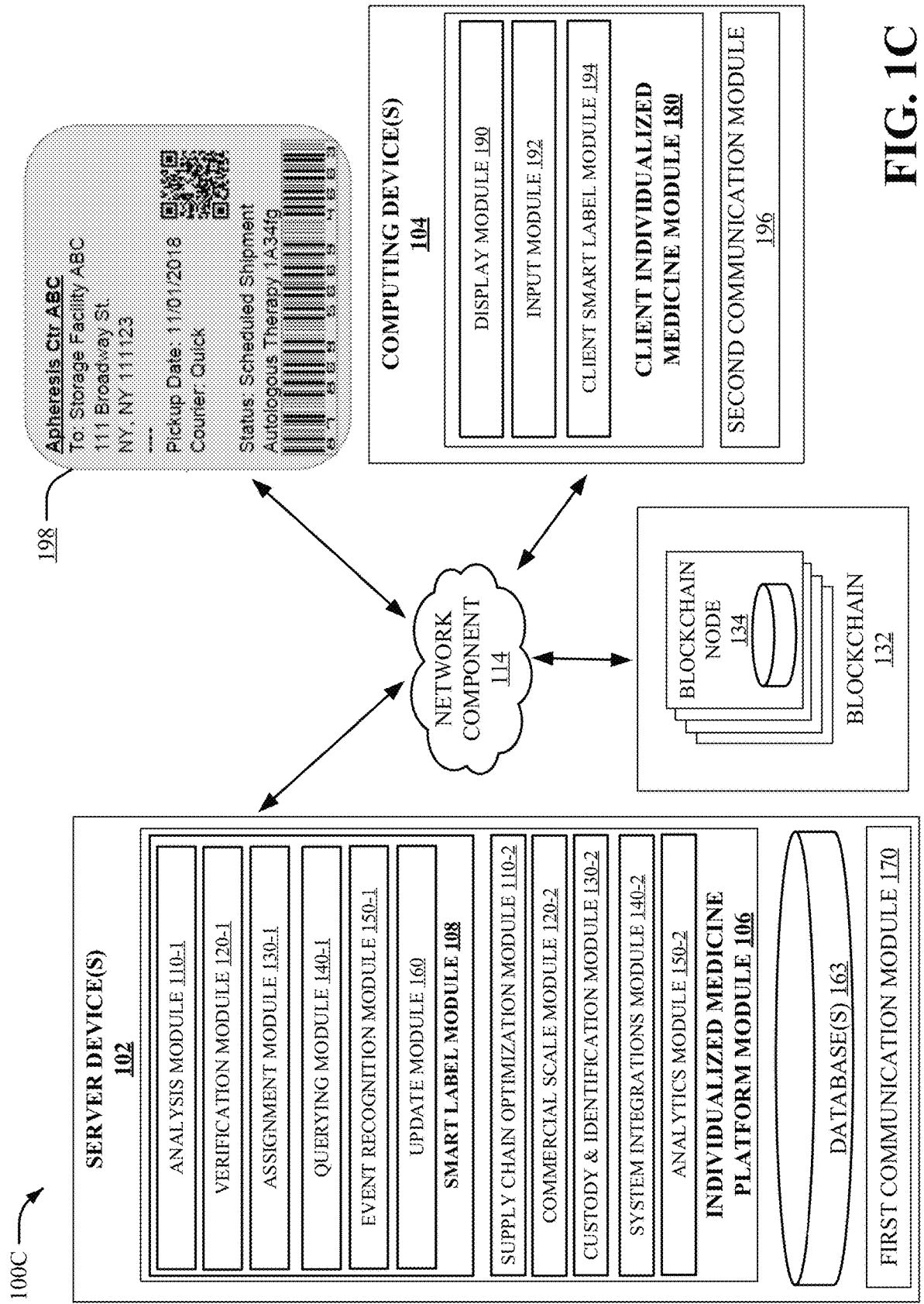
FIG. 1C illustrates an example, non-limiting block diagram of a representative environment comprising server device(s), computing device(s) smart label devices, and blockchain store in which data associated with a personalized medicine supply chain platform and a smart label system can be generated, transmitted and stored in accordance with one or more embodiments described herein.

Turning now to FIG. 1C, illustrated is an example, non-limiting block diagram of a representative environment 100C comprising server device(s) 102, computing device(s) 104, smart label device(s) 198, and blockchain store in which data associated with a personalized medicine supply chain platform and a smart label system can be generated, transmitted and stored in accordance with one or more embodiments described herein. Repetitive description of like elements employed in other embodiments described herein is omitted for sake of brevity.

In an aspect, environment 100C can include or otherwise be associated with one or more server device(s) 102 that can execute individualized medicine platform module 106, smart label module 108, analysis module 110-1, verification module 120-1, assignment module 130-1, querying module 140-1, event recognition module 150-1, update module 160, and first communication module 170. Furthermore, server device(s) 102 can comprise database(s) 163. Environment 100C can also include computing device(s) 104 that employs client individualized medicine module 180, client smart label module 194, input module 192, display module 190, and second communication module 196. Environment 100C can also include network component 114 and smart label device(s) 198. Furthermore, in an aspect, Environment 100C can include blockchain 132 and blockchain node 134.

In an aspect, blockchain 132 can be generated in accordance with one or more implementation disclosed herein. Furthermore, blockchain 132 can comprise blockchain node(s) 134. In a non-limiting embodiment, environment 100C can be configured to communicate and/or integrate with a distributed blockchain system comprising multiple computing nodes, such that each computing node is configured to store a copy or a portion of a blockchain. In some instances, a blockchain 320 may be used to store data associated with individualized medicine platform module 106, smart label device(s) 198, smart label module 108 and other such devices in environment 100C. Furthermore, in an aspect, blockchain 132 can be a distributed database that maintains a continuously updated list of records (e.g., list of smart label device locations, smart label device sensor data, smart label device data user authentication data, geo-fencing location data, specimen condition data, cryogenic storage temperature data, courier data, etc.) where each the updated list of records can be stored on blocks linked together as a chain. In an aspect, the blocks can be secure storage vehicles (e.g., encryption based on public-key and private-key pairings) and are immutable (cannot be changed).

In another aspect, the blockchain 132 can record a transaction (e.g., a transfer of information onto, from or with individualized medicine platform module 106, smart label module 108, smart label device(s) 198) within a ledger database of the blockchain 132 that is shared by devices participating in a distributed network of computers. In yet another aspect, the distributed ledger can present a consensual (by all computers within the distributed network) record corresponding to a cryptographic audit trail that is validated and maintained by independent computers. In yet another aspect, blockchain 132 can employ a network of blockchain nodes 134 that can support the blockchain, which may include a set of blocks that store data corresponding to individualized medicine platform module 106.

In an aspect, data stored on nodes of blockchain 132 can include transactional data (e.g., event data, identifier data, smart label device(s) 198 data, location data, custody data, triggering event data, etc.) acquired, generated, curated, transformed, and/or received by individualized medicine platform module 106. In a non-limiting aspect, the data can be transmitted as duplicate data to a blockchain system employing blockchain 132. In another non-limiting aspect, the data can be transmitted to the blockchain system as original data (non-duplicate data), such that the blockchain system serves as a primary data store for one or more sets of data. In an embodiment, only the additional data in a transaction (not including the previously transmitted duplicate data) can be transmitted for incorporation onto the blockchain.

As such, the blockchain can be configured to store data corresponding to the data of individualized medicine platform module 106, smart label module 108, and/or smart label device(s) 198. In an aspect, blockchain 132 is a data structure that stores a list of transactions. In an aspect, blockchain 132 can be a distributed electronic ledger that records transactions between various stakeholders (e.g., providers, patients, centers of excellence, couriers or third-party logistics providers, manufacturers, suppliers, cryogenic storage facilities, administrative managers, and other such stakeholders) of the individualized medicine platform module 106. In one or more non-limiting embodiments, blockchain 132 can be a decentralized public (or private) transaction ledger that can be deployed over one or more node (e.g., server) and configured to perform transaction-based state transitions and smart contract functionality.

In a non-limiting implementation, computing device(s) 104 can interact with a server device(s) 102 configured to control one or more node (e.g., blockchain node 134 and other such nodes) of blockchain 132. In an aspect, server device (s) 102 can be configured to facilitate access to one or more node of blockchain 132. For instance, server device(s) 102 can control access to blockchain node 134 that represents an Ethereum blockchain or other distributed ledger node featuring transaction-based state transitions and/or smart contract functionality. In another aspect, a smart contract may be stored as a block with blockchain 132 and data included as components of the smart contract can be stored within separate blocks within the blockchain. Furthermore, in a non-limiting embodiment, each node of a blockchain 320 can store a copy of a smart contract program structures. In an aspect, environment 100C allows for a communication between any individual device(s) in environment 100C and blockchain 132. In other non-limiting embodiments, blockchain communication routes can be limited between select devices.

Figure 1D:
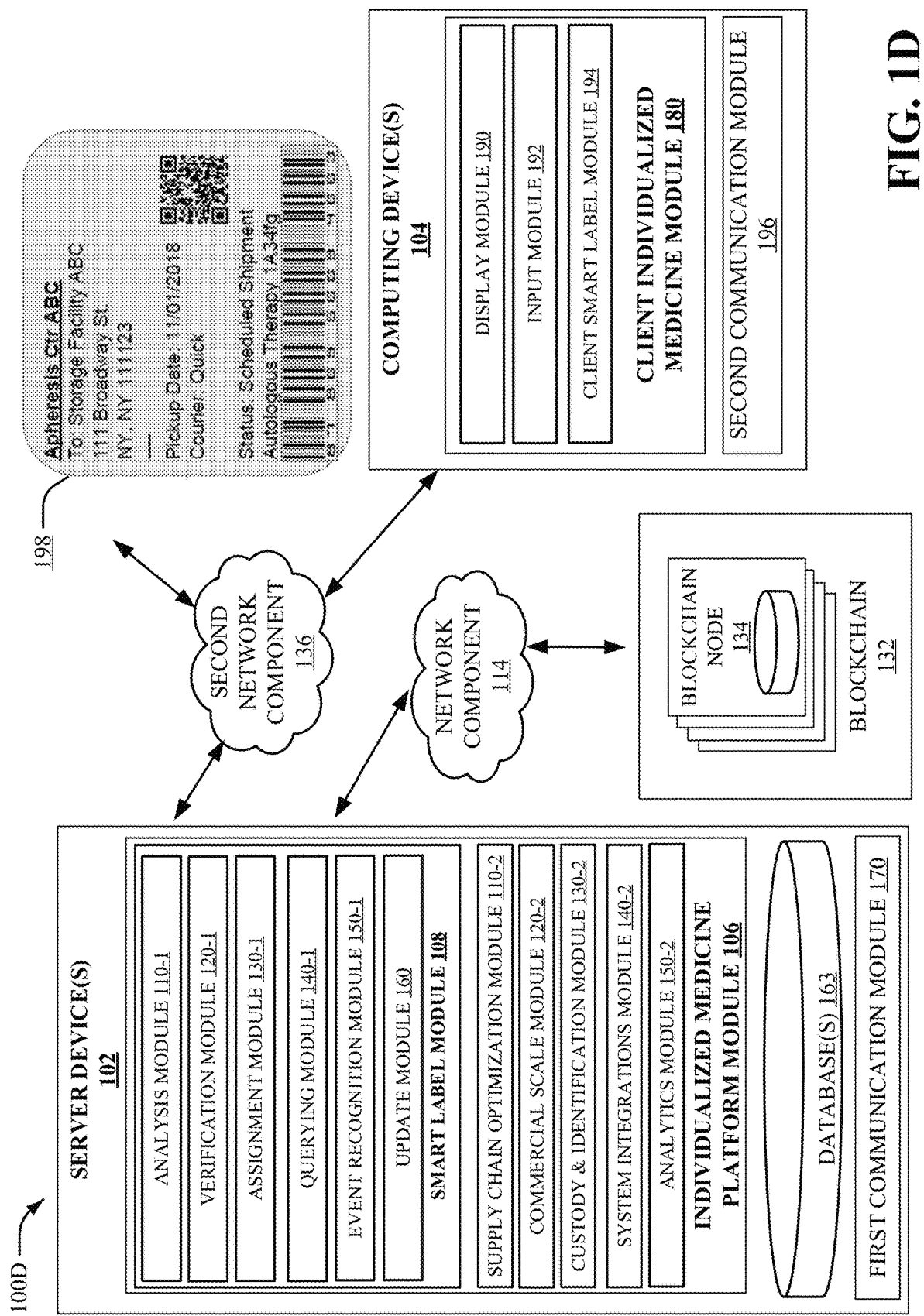
FIG. 1D illustrates an example, non-limiting block diagram of a representative environment comprising server device(s), computing device(s) smart label devices, and blockchain store in which data associated with a personalized medicine supply chain platform and a smart label system can be generated, transmitted and stored in accordance with one or more embodiments described herein.

FIG. 1D illustrates an example, non-limiting block diagram of a representative environment 100D comprising server device(s) 102, computing device(s) 104 smart label devices 198, and blockchain store in which data associated with a personalized medicine supply chain platform and a smart label system can be generated, transmitted and stored in accordance with one or more embodiments described herein. Repetitive description of like elements employed in other embodiments described herein is omitted for sake of brevity.

In an aspect, environment 100D can include or otherwise be associated with one or more server device(s) 102 that can execute individualized medicine platform module 106, smart label module 108, analysis module 110-1, verification module 120-1, assignment module 130-1, querying module 140-1, event recognition module 150-1, update module 160, and first communication module 170. Furthermore, server device(s) 102 can comprise database(s) 163. Environment 100D can also include computing device(s) 104 that employs client individualized medicine module 180, client smart label module 194, input module 192, display module 190, and second communication module 196. Environment 100C can also include network component 114 and smart label device(s) 198. Furthermore, in an aspect, Environment 100D can include blockchain 132 and blockchain node 134. In another aspect, environment 100D can include second network component 136.

In an aspect, environment 100D can employ network component 114 that facilitates communication between blockchain 132 and central service provider device such as server device(s) 102. Furthermore, second network component 136 can facilitate communication between all server device(s) 102, computing device(s) 104, and smart label device(s) 198 in environment 100D. In an aspect, network component 114 and second network component 136 can comprise at least the same functionality as network component 114. Environment 100D allows for server device(s) 102 along with smart label module 108 and/or individualized medicine platform module 106 to be configured as the central authority to write data (including integrated data from third party systems integrated with individualized medicine platform module 106 and smart label module 108) to blockchain 132.

As such, smart label module 108 and/or individualized medicine platform module 106 can provide access to a primary transaction record stored on blockchain 132 to which any stakeholders, users, and others can execute smart contracts, perform chain of identity data audits, perform chain of custody data audits, and/or generally access records. In yet another aspect, smart label module 108 and/or individualized medicine platform module 106 can provide access to more than one blockchain 132. For instance, a first blockchain can store only transaction data associated with courier events and a second blockchain can store only transaction data associated with manufacturing events such that relevant stakeholder devices can access respective blockchains. As such, environment 100D allow server device(s) 102 to control the access and writing onto the blockchain 132.

Furthermore, encryption mechanisms can be provided to allow access to only authorized data on the immutable blockchain based on authorization credentials. As a non-limiting example, a stakeholder device utilizing smart label module 108 and/or individualized medicine platform module 106 can read data stored on blockchain 132 and the smart label module 108 and/or individualized medicine platform module 106 can write data to the blockchain 132 (e.g., append data to the blockchain 320). In yet another aspect, a node on the blockchain 132 can validate or remove transactions deemed to be invalid as well as determine an ordering of remaining valid transactions to be appended to the blockchain 132 as part of a new block. In an aspect, upon the generation of a new block (e.g., that has been validated), the data within the new block is immutable (e.g., cannot be modified or altered). In a non-limiting embodiment, one or more validation nodes associated with blockchain 132 can be validated in accordance with validation rules stored within the validation nodes, such rules including syntax requirements of data, specification of events or tasks a data contributor to the blockchain can perform, and other such rules. In a non-limiting embodiment, smart label module 108 and/or individualized medicine platform module 106 can configure the validation nodes and set of rules.

Figure 2A:
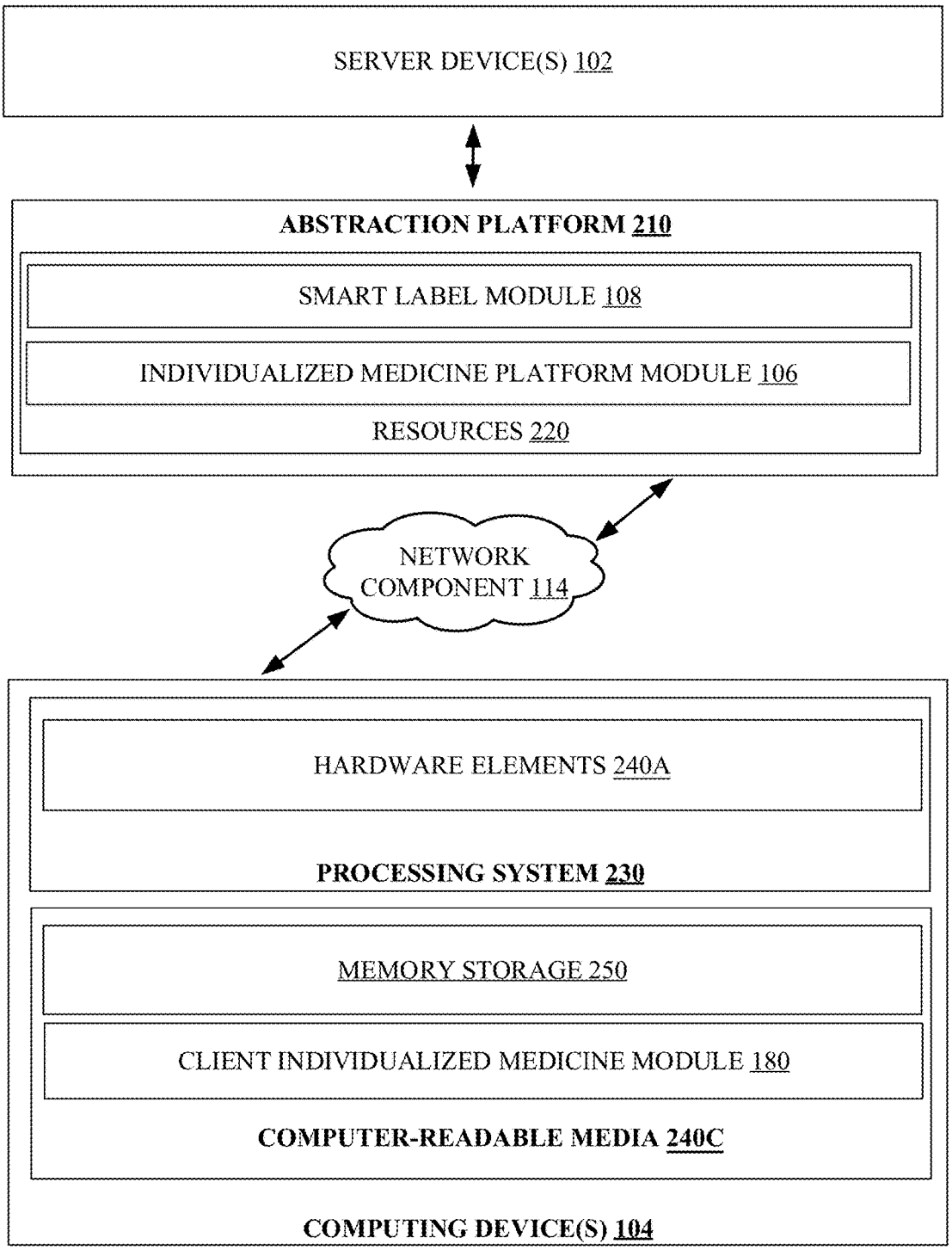
FIG. 2A illustrates an example, non-limiting environment in which cloud-based services can be used to provide features corresponding to events and activities associated with a smart label module platform in accordance with one or more embodiments described herein.

Turning now to FIG. 2A, illustrated is an example environment 200A in accordance with one or more implementations. In various implementations, the example described with respect to FIG. 2A can be considered a continuation of the examples described in FIG. 1B-FIG. 1D. Repetitive description of like elements employed in other embodiments described herein is omitted for sake of brevity. It should be understood that the layers depicted are intended to be illustrative only and embodiments of the invention are not limited thereto. FIG. 2A illustrates an example, non-limiting environment 200A in which cloud-based services can be used to provide features corresponding to events and activities associated with an individualized medicine platform module 106 and/a smart label module 108 platform in accordance with one or more embodiments described herein. In an aspect, environment 200A can include server device(s) 102, computing device(s) 104, and network component 114, where computing device(s) 104 includes a processing system 230, and one or more computer-readable media 240C.

In an aspect, processor 230 can comprise one or more processor configured to perform one or more operations (of at least one module of client individualized medicine module 180) using hardware. As such, processor 230 can include hardware elements 240A that may be configured as processors, functional blocks, and so forth. This may include implementation in hardware as an application specific integrated circuit or other logic device formed using one or more semiconductors. In an aspect, the hardware elements 240A are not limited by the materials from which they are formed, or the processing mechanisms employed by such materials. For example, processors may be comprised of semiconductor(s) and/or transistors (e.g., electronic integrated circuits). In such a context, processor-executable instructions may be electronically executable instructions.

The computer-readable media 240C is illustrated as including memory storage 250. The memory storage 250 represents memory storage capacity associated with one or more computer-readable media. The memory storage 250 may include volatile media (such as random-access memory (RAM)) and/or nonvolatile media (such as read only memory (ROM), Flash memory, optical disks, magnetic disks, and so forth). The memory storage 208 may include fixed media (e.g., RAM, ROM, a fixed hard drive, and so on) as well as removable media (e.g., Flash memory, a removable hard drive, an optical disc, and so forth). The computer-readable media 240C may be configured in a variety of other ways as further described below. In an aspect, client individualized medicine module 180 of FIG. 1 is illustrated as residing within memory storage 250, but alternate or additional implementations can implement client individualized medicine module 180 using combinations of firmware, hardware, and/or software without departing from the scope of the claimed subject matter, such as hardware elements 240A.

Example environment 200 can enable multiple devices to be interconnected through server device(s) 102, where server device(s) 102 can be local to the multiple devices, remote from the multiple devices, or any combination thereof. In one or more implementations, server device(s) 102 can be configured as a cloud of one or more server computers that are connected to the multiple devices through a network (e.g., using network component 114), the Internet, or other data communication link capable of enabling functionality to be delivered across multiple devices (e.g., several smartphone devices, desktops, tablets, etc.) to provide a common and seamless experience to a user of the multiple devices. Each of the multiple devices may have different physical requirements and capabilities, and the central computing device uses a platform to enable the delivery of an experience to the device that is both tailored to the device and yet common to all devices. In a non-limiting embodiment, a class of target devices having unique physical features, types of usage or other such characteristics can be deployed, and tailored user experiences can be implemented on such class of generic class of devices.

In an aspect, cloud computing network or network component 114 can include or represent an abstraction platform 210 for resources 220. In another aspect, the abstraction platform 212 abstracts underlying functionality of hardware (e.g., servers) and software resources of the cloud 210. In an aspect, resources 220 may include applications and/or data that can be utilized while computer processing is executed on servers (e.g., server device(s) 102) that are remote from the computing device(s) 104. For example, resources 220 can include individualized medicine platform module 106 at FIG. 1A. In another aspect, the abstraction platform 210 may abstract resources and functions to connect computing device 104 with other computing devices and may also serve to abstract scaling of resources to provide a corresponding level of scale to encountered demand for the resources 220 that are implemented via the abstraction platform 210. Accordingly, in an interconnected device embodiment, implementation of functionality described herein may be distributed throughout the system. For example, the functionality may be implemented in part on the computing device 104 as well as via the abstraction platform 210 that abstracts the functionality of the network component 114.

In another aspect, abstraction platform 212 can allow for external system integrators to keep data private on individualized medicine platform module 106, while abstraction platform 210 can extract learnings from such data to educate a range of machine learning algorithms. For instance, hyperparameters of machine learning models applied to a first external device data can be extracted and the hyper-parameters can be applied to data of a second external device. As such, learnings from analyzing and curating a first client data can be applied to the analysis and curation of a second client data without ever exposing the private data of each user.

Figure 2B:
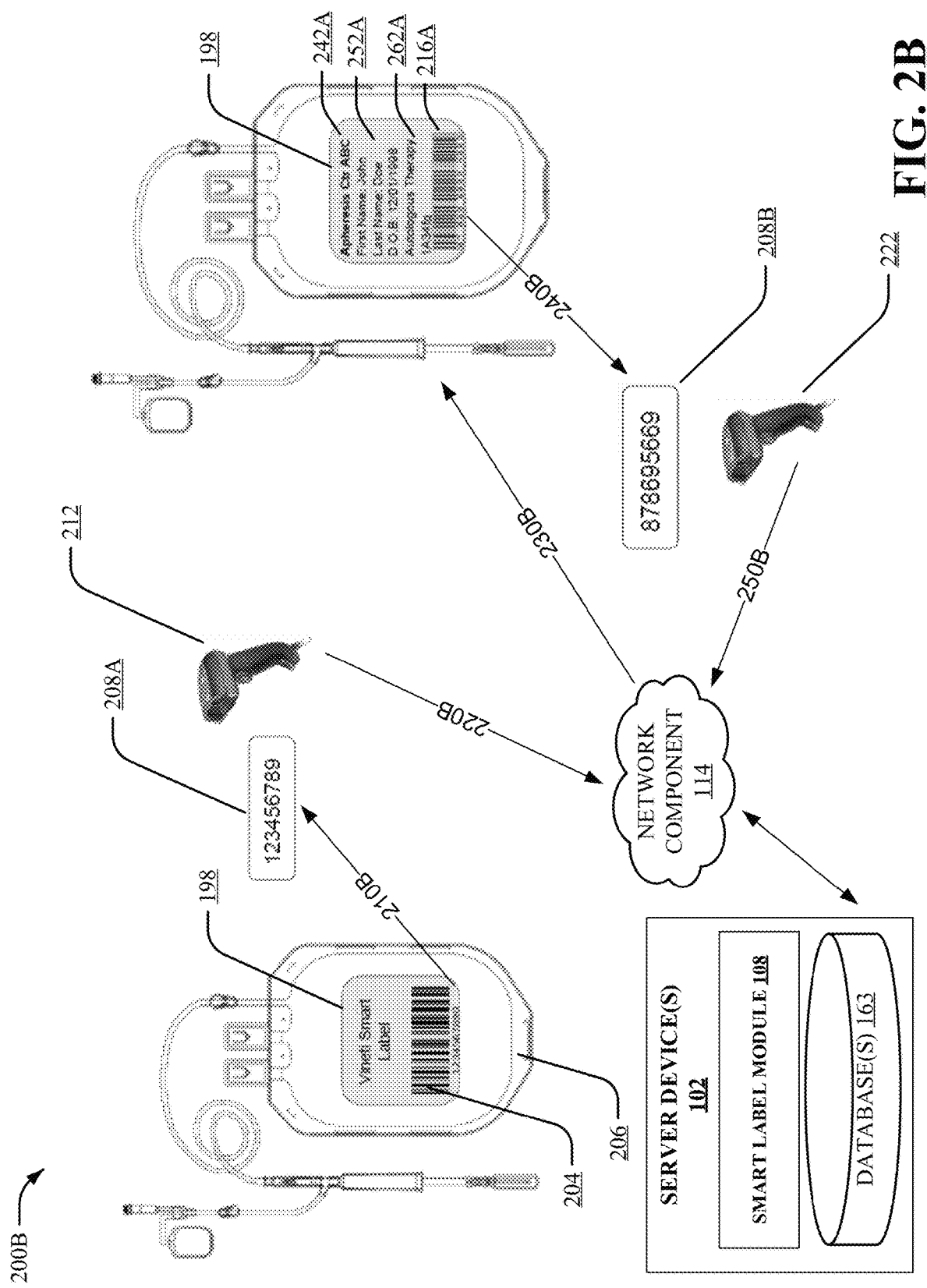
FIG. 2B illustrates an example, non-limiting diagram of a smart label device and a sample collection process in accordance with one or more embodiments described herein.

Turning now to FIG. 2B, illustrated is an example, non-limiting diagram 200B of smart label device(s) 198 and a sample collection process in accordance with one or more embodiments described herein. Repetitive description of like elements employed in other embodiments described herein is omitted for sake of brevity.

In an aspect, disclosed is a non-limiting embodiment of a collection process such as with respect to collection of patient-specific starting material that will be used to manufacture a final drug product for infusion. At a collection center, a patient specimen and identification information can be collected. At reference numeral 206 a patient sample can be collected in blood bag 206 which corresponds to smart label device(s) 198. In an aspect, smart label device(s) 198 can display first identifier 204 (e.g., bar code, QR code, etc.). In some non-limiting implementations, first identifier 204 can be scanned (e.g., via first scanner 212 operated by a staffer such as a nurse) and label identification data 208A can be accordingly transmitted (via network component 114) into a collection component of smart label module 108.

At reference numeral 210B, label identification data 208A is scanned. At reference numeral 220B, label identification data 208A is transmitted via network component 114 to smart label module 108 of server device(s) 102. Furthermore, smart label module 108 can verify (e.g., using verification module 120-1) first label identification data 208A and assign (e.g., using assignment module 130-1) such data to patient identification data (e.g., patient name, date of birth, specimen description, etc.). Upon verification of such label identification data 208A, the data can be stored at stored at database(s) 163 or blockchain 132. Accordingly, such data recordation (e.g., using event recognition module 150-1) can represent an occurrence of a first chain of custody event and/or chain of identity event for the smart label device(s) 198 and corresponding specimen.

In some non-limiting embodiments, smart label module 108 can query (e.g., using querying module 140-1) smart label device(s) 198 for location data. For instance, based upon a query for location data, analysis module 110-1 can acquire GPD coordinate data from smart label device(s) 198 and verify (e.g., using verification module 120-1) that smart label device(s) 198 is located in the correct location. Furthermore, in a non-limiting embodiment, based on the verification, smart label module 108 can transmit (e.g., using update module 160) updated label data for display at smart label device(s) 198. In an aspect, the updated label data can include patient information and/or a newly generated second identifier 216A that can represent a new identifier (e.g., new barcode data, new QR code data, etc.). Furthermore, in an aspect, smart label device(s) 198 can be include updated facility data 242A, updated personal health information data 252A (e.g., patient first and last name, date of birth, social security, patient address, etc.), updated descriptive data 262A (e.g., therapy type), newly generated second identifier 216A, and/or other such information. The smart label device(s) 198 can be de-identified (e.g., remove patient PHI) and re-identified (e.g., inclusion of PHI and other identifiers) based on various rules (e.g., facility authorizations, user authorizations, facility policies, etc.). For instance, an infusion center nurse may need to view PHI on a smart label device(s) 198 to confirm that they are infusing a therapeutic corresponding to the correct patient.

In another aspect, at reference numeral 240B, second identifier 216A can be re-scanned (e.g., via second scanner 222) and second label identification data 208B (e.g., scanned from the new barcode) can be transmitted (e.g., indicated by reference numeral 250B), via network component 114, to smart label module 108 of server device(s) 102. Furthermore, in an aspect, smart label module 108 can verify (e.g., using verification module 120-1) second label identification data 208B and event recognition module 150-1 can transmit the second label identification data 208B as a second chain of identity event or second chain of custody event. Also, the second label identification data 208B can be recorded at blockchain 132 and/or database(s) 163.

Figure 3A:
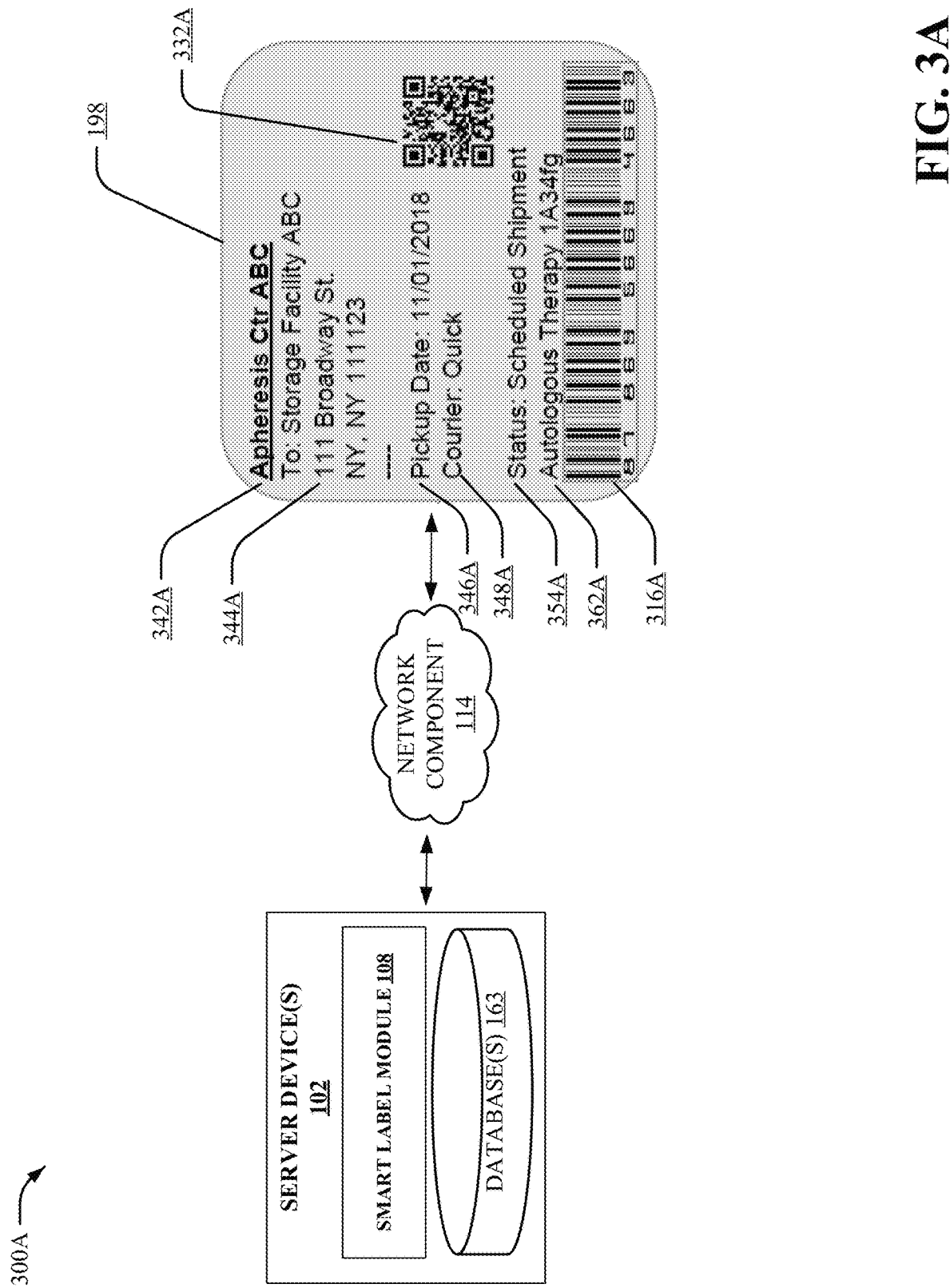
FIG. 3A illustrates an example, non-limiting diagram of a smart label device and a sample shipment process in accordance with one or more embodiments described herein.

Turning now to FIG. 3A, illustrated is an example, non-limiting diagram of environment 300A that includes smart label device(s) 198 and a sample shipment process in accordance with one or more embodiments described herein. Repetitive description of like elements employed in other embodiments described herein is omitted for sake of brevity.

At environment 300A, smart label device(s) 198 can receive updated label content based on a receipt of schedule data represent pickup scheduling instructions by a courier. Furthermore, in an aspect, a user can utilize input module 192 of client individualized medicine module 180 to perform scheduling requests. In another aspect, smart label module 108 can transmit, via network component 114, updated (e.g., using update module 160) label data that can include sender facility 342A, destination facility 344A (e.g., address), pickup data 346A (e.g., pickup date), courier identifier 348A, first shipment status 354A (e.g., shipped, in transit, etc.), therapy identifier 362A, third identifier 316A, and/or fourth identifier 322A (e.g., QR code).

Figure 3B:
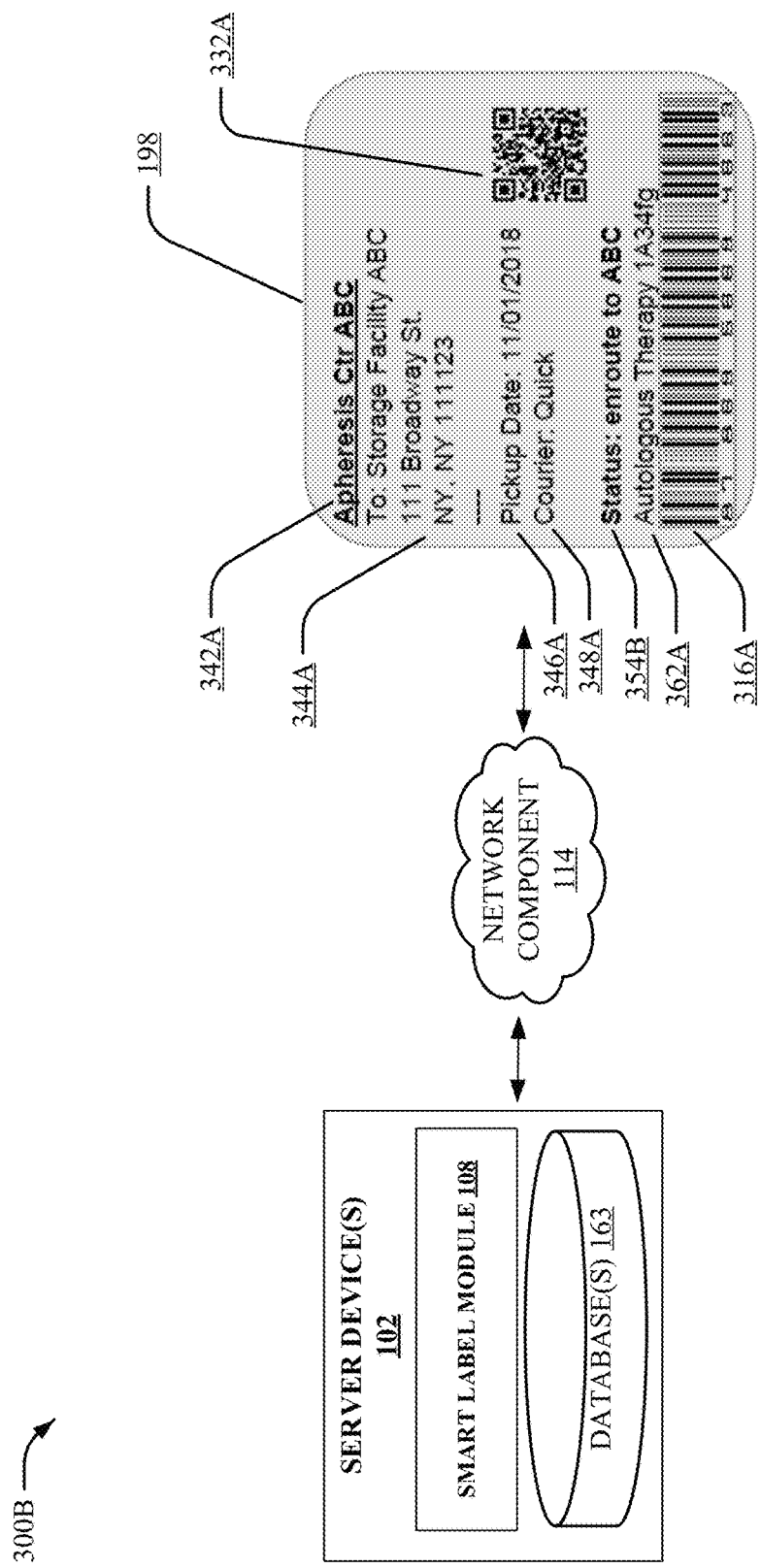
FIG. 3B illustrates an example, non-limiting diagram of a smart label device and a change of custody event in accordance with one or more embodiments described herein.

Turning now to FIG. 3B, illustrated is an example, non-limiting diagram of environment 300B that includes a smart label device(s) 198 and a change of custody event in accordance with one or more embodiments described herein. Repetitive description of like elements employed in other embodiments described herein is omitted for sake of brevity.

At environment 300B, smart label device(s) 198 can receive updated label content based on an occurrence of a change of custody event such as a courier picking up a specimen (e.g., taking possession of the specimen with smart label device(s) 198). Furthermore, smart label module 108 can verify (e.g., using verification module 120-1) courier authentication information and accordingly transmit update (e.g., using update module 160) label data to smart label device(s) 198 based on the verification event occurring and chain of custody event occurring. Furthermore, in an aspect, smart label module 108 can transmit, via network component 114, updated (e.g., using update module 160) label data that can include sender facility 342A, destination facility 344A (e.g., address), pickup data 346A, courier identifier 348A, second shipment status 354B (e.g., specimen in route, etc.), therapy identifier 362A, third identifier 316A, and/or fourth identifier 322A (e.g., QR code). For instance, smart label module 108 can transmit updated data to smart label device(s) 198 such that second shipment status 354B is updated to represent the status of the courier (e.g., courier picked up patient material from apheresis center).

FIG. 3C illustrates an example, non-limiting diagram of environment 300C that includes a smart label device(s) 198 and a change of label content data in accordance with one or more embodiments described herein. Repetitive description of like elements employed in other embodiments described herein is omitted for sake of brevity.

At environment 300C, live label data can be dynamically transmitted and displayed at smart label device(s) 198 at any given time (e.g., during manufacturing). For instance, smart label device(s) 198 can be affixed to a raw material (e.g., blood sample bag) and dynamic information corresponding to the blood bag can be displayed on smart label device(s) 198. In an aspect, smart label device(s) 198 can display current custodian data 364C (e.g., name of custodian), current machine 366C (e.g., name of equipment used for manufacture), current time data 368C (e.g., timing), previous machine 372C (e.g., name of previous equipment used in last manufacturing step), last custodian data 374C (e.g., name of previous custodian), status indicator 354C (e.g., operation being performed such as "manufacturing occurring by machine XYZ"), and/or therapy identifier 362A.

Furthermore, in an aspect, smart label module 108 can transmit, via network component 114, updated (e.g., using update module 160) label data that can include sender facility 342A, destination facility 344A (e.g., address), pickup data 346A, courier identifier 348A, second shipment status 354B (e.g., specimen en route, etc.), therapy identifier 362A, third identifier 316A, and/or fourth identifier 322A (e.g., QR code). For instance, smart label module 108 can transmit updated data to smart label device(s) 198 such that second shipment status 354B is updated to represent the status of the courier (e.g., courier picked up patient material from apheresis center).

Figure 3D:
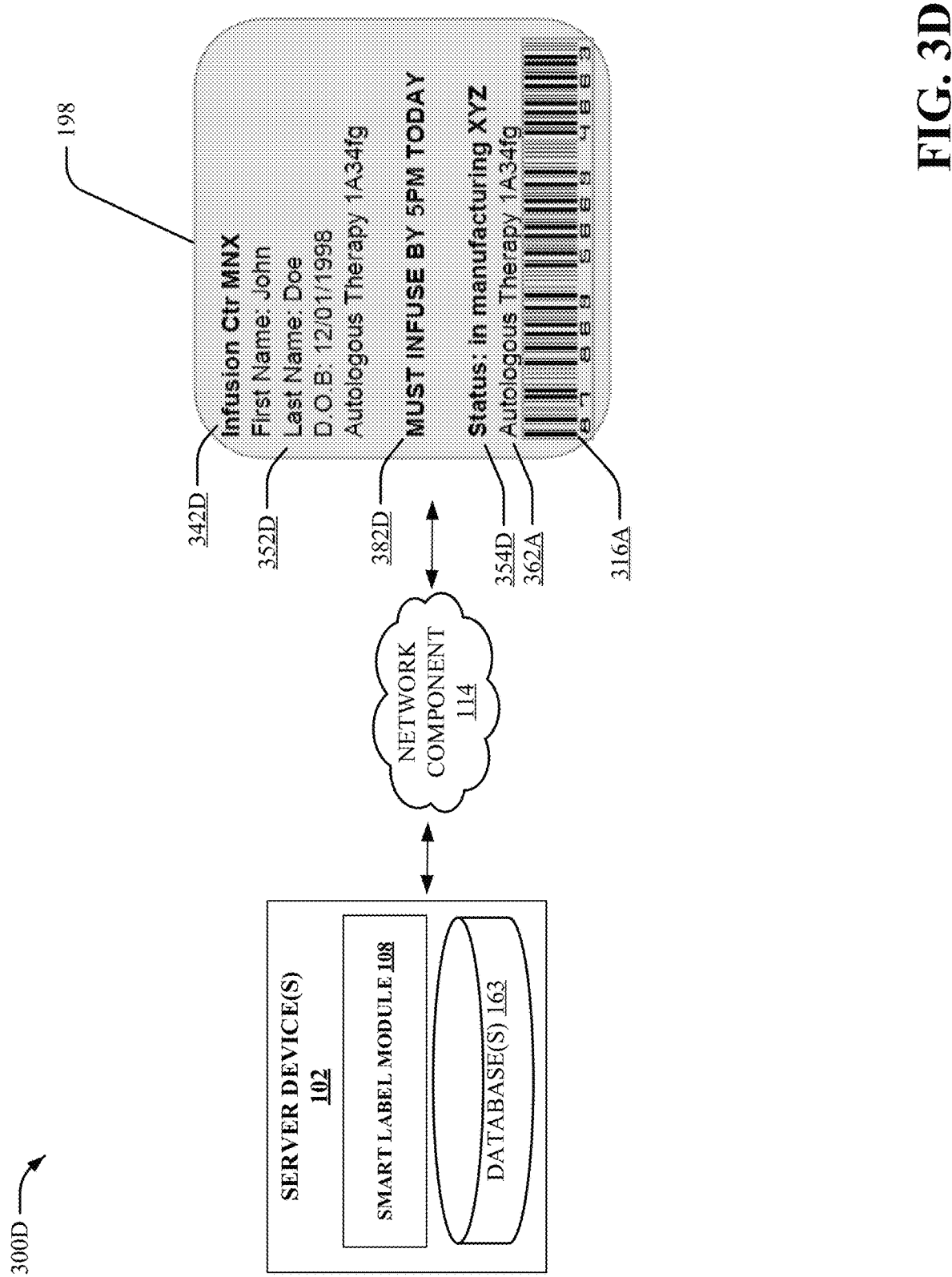
FIG. 3D illustrates an example, non-limiting diagram of a smart label device and a change of label content data in accordance with one or more embodiments described herein.

FIG. 3D illustrates an example, non-limiting diagram of environment 300D that includes a smart label device(s) 198 and a change of label content data in accordance with one or more embodiments described herein. Repetitive description of like elements employed in other embodiments described herein is omitted for sake of brevity.

At environment 300D, smart label module 108 can transmit PHI data to be redisplayed at smart label device(s) 198. Furthermore, verification data can be transmitted (e.g., via an authenticated device or user) to smart label module 108 to confirm the display of the PHI at smart label device(s) 198. In another aspect, smart label module 108 can transmit instruction data for display at smart label device(s) 198 such as a deadline time a sample should be infused. In an aspect, smart label module 108 can transmit (e.g., via network component 114) updated data that includes infusion facility 342D, protected health information 352D, instructions 382D (e.g., infusion instructions), manufacturing status 354D, therapy identifier 362A, and third identifier 316A.

Figure 4:
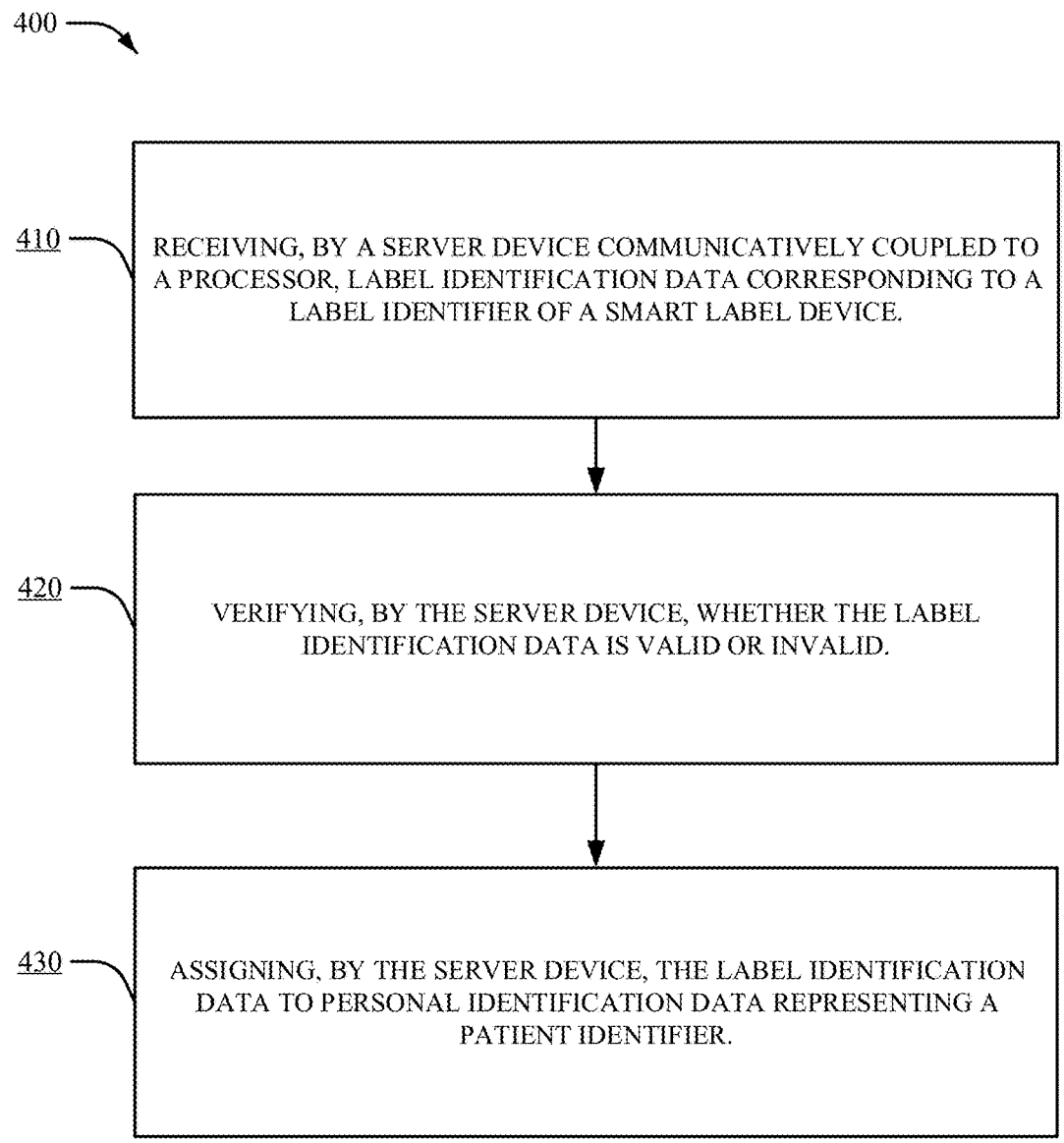
FIG. 4 illustrates a flow diagram of an example, non-limiting computer-implemented method 400 for assigning label identification data to personal identification data in accordance with one or more embodiments described herein.

FIG. 4 illustrates a flow diagram of an example, non-limiting computer-implemented method 400 for assigning label identification data to personal identification data in accordance with one or more embodiments described herein. Repetitive description of like elements employed in other embodiments described herein is omitted for sake of brevity.

In an aspect, one or more of the components and/or modules described in computer-implemented method 400 can be electrically and/or communicatively coupled to one or more devices. In some implementations, at reference numeral 410, a server device communicatively coupled to a processor, receives (e.g., using analysis module 110-1) label identification data corresponding to a label identifier of a smart label device. At reference numeral 420, the server device verifies (e.g., using verification module 120-1) whether the label identification data is valid or invalid. At reference numeral 430, the server device assigns (e.g., using assignment module 130-1) the label identification data to personal identification data representing a patient identifier.

Figure 5:
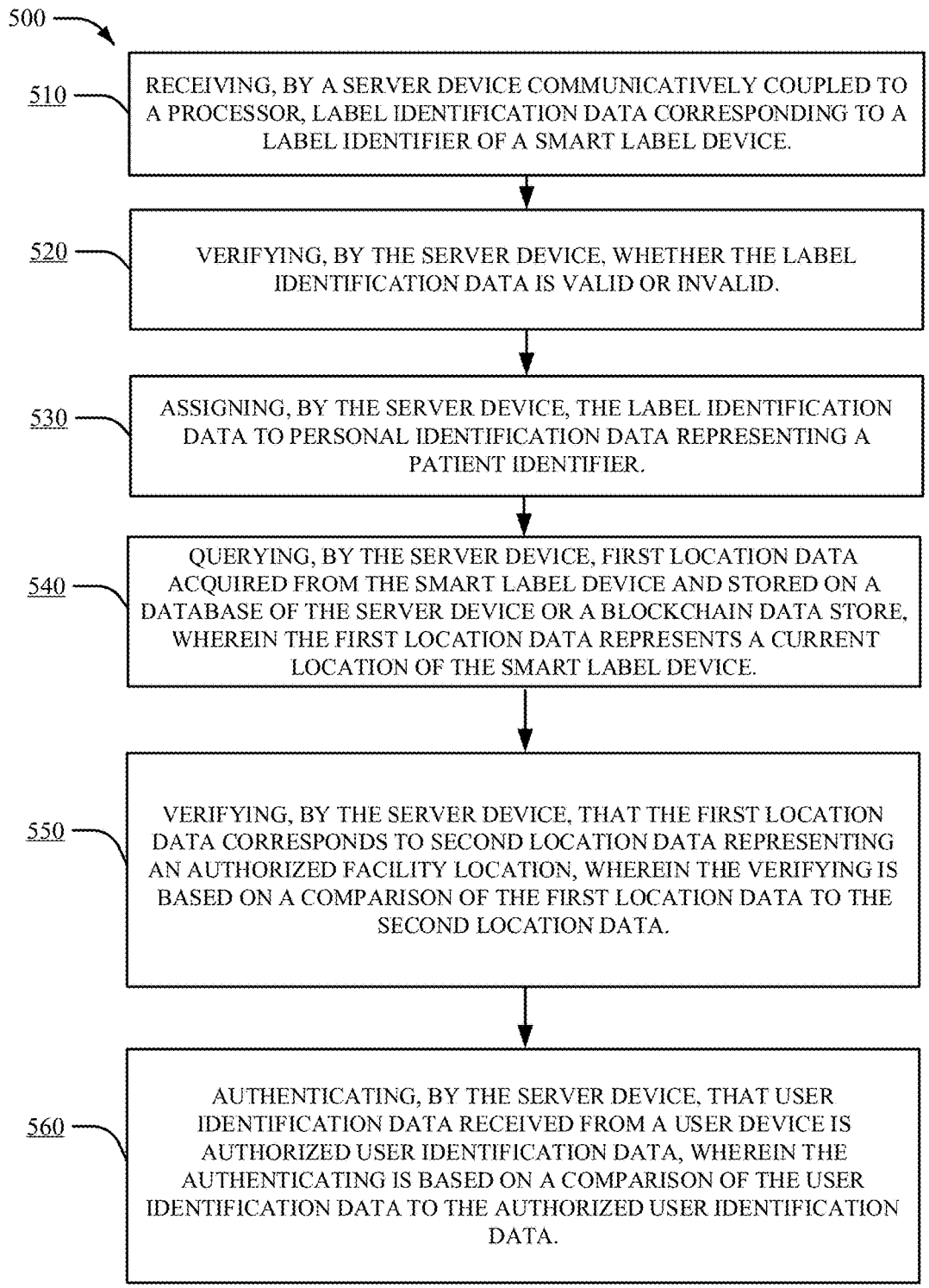
FIG. 5 illustrates a flow diagram of an example, non-limiting computer-implemented method 500 for verifying an authorized facility identity based on location data of the smart label device in accordance with one or more embodiments described herein.

FIG. 5 illustrates a flow diagram of an example, non-limiting computer-implemented method 500 for verifying an authorized facility identity based on location data of the smart label device(s) 198 in accordance with one or more embodiments described herein. Repetitive description of like elements employed in other embodiments described herein is omitted for sake of brevity.

In an aspect, one or more of the components and/or modules described in computer-implemented method 500 can be electrically and/or communicatively coupled to one or more devices. In some implementations, at reference numeral 510, a server device communicatively coupled to a processor, receives (e.g., using analysis module 110-1) label identification data corresponding to a label identifier of a smart label device. At reference numeral 520, the server device verifies (e.g., using verification module 120-1) whether the label identification data is valid or invalid. At reference numeral 530, the server device assigns (e.g., using assignment module 130-1) the label identification data to personal identification data representing a patient identifier.

At reference numeral 540, the server device queries (e.g., using querying module 140-1) first location data acquired from the smart label device and stored on a database of the server device or a blockchain data store, wherein the first location data represents a current location of the smart label device(s) 198. At reference numeral 550, the server device verifies (e.g., using verification module 120-1) that the first location data corresponds to second location data representing an authorized facility location, wherein the verifying is based on a comparison of the first location data to the second location data. At reference numeral 560, the server device (e.g., server device(s) 102) authenticates that user identification data received from a user device is authorized user identification data, wherein the authenticating is based on a comparison of the user identification data to the authorized user identification data.

Figure 6:
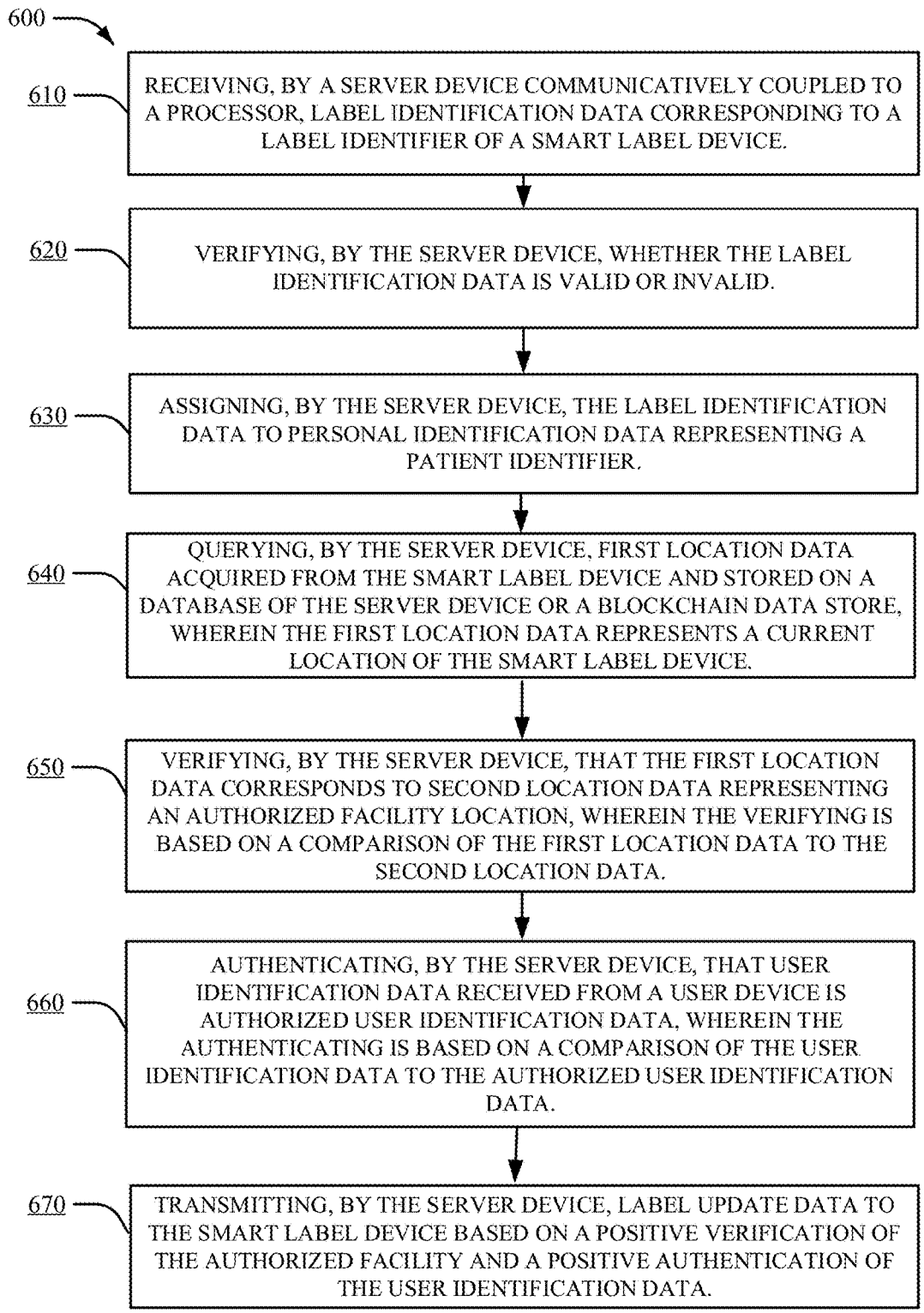
FIG. 6 illustrates a flow diagram of an example, non-limiting computer-implemented method 600 for transmitting label update data to the smart label device based on a positive authentication in accordance with one or more embodiments described herein.

FIG. 6 illustrates a flow diagram of an example, non-limiting computer-implemented method 600 for transmitting label update data to the smart label device(s) 198 based on a positive authentication in accordance with one or more embodiments described herein. Repetitive description of like elements employed in other embodiments described herein is omitted for sake of brevity.

In an aspect, one or more of the components and/or modules described in computer-implemented method 600 can be electrically and/or communicatively coupled to one or more devices. In some implementations, at reference numeral 610, a server device communicatively coupled to a processor, receives (e.g., using analysis module 110-1) label identification data corresponding to a label identifier of a smart label device. At reference numeral 620, the server device verifies (e.g., using verification module 120-1) whether the label identification data is valid or invalid. At reference numeral 630, the server device assigns (e.g., using assignment module 130-1) the label identification data to personal identification data representing a patient identifier.

At reference numeral 640, the server device queries (e.g., using querying module 140-1) first location data acquired from the smart label device and stored on a database of the server device or a blockchain data store, wherein the first location data represents a current location of the smart label device(s) 198. At reference numeral 650, the server device verifies (e.g., using verification module 120-1) that the first location data corresponds to second location data representing an authorized facility location, wherein the verifying is based on a comparison of the first location data to the second location data. At reference numeral 660, the server device (e.g., server device(s) 102) authenticates that user identification data received from a user device is authorized user identification data, wherein the authenticating is based on a comparison of the user identification data to the authorized user identification data.

At reference numeral 670, the server device transmits (e.g., using update module 150) label update data to the smart label device based on a positive verification of the authorized facility and a positive authentication of the user identification data. In some non-limiting embodiments, the method can also include transmitting (e.g., using event recognition module 150-1), by the server device(s) 102, the first location data or the user identification data to a data store, wherein the data store is a blockchain data store or the database(s) 163 of the server device, wherein first location data recorded at the data store represents a chain of custody event, and wherein the user identification data recorded at the data store represents a chain of identity event.

In other methods, non-limiting computer-implemented methods can include accessing, via a client device, a smart label control system; sending, using the client device, a trigger event to the smart label analytics system to perform a query analysis; receiving, from the smart label control system, smart label data comprising at least one of geo-location coordinates, chain of identity information, chain of custody information; and outputting, from the smart label control system, rendered analytics based on the smart label data. Furthermore, the method can further comprise receiving input to configure the smart label device based on a set of configuration criteria, wherein the set of configuration criteria comprises at least one of a geo-location recognition configuration, authentication configuration, validation configuration, or smart label display configuration.

In another aspect, the method can further comprise generating, by the smart label control system, drill-up media content or drill-down media content based, at least in part, on metadata associated with the smart label data; performing, by the smart label control system, a drill-up operation or a drill-down operation based on control input by the client device; and outputting a rendering of the drill-up media content or the drill-down media content based on the control input. Also, in an aspect, the method can further comprise receiving, by the smart label control system, detection data from the smart label device, wherein the detection data represents a geo-locational boundary signal; and disabling, by the smart label control system, a rendering of content on a display of the smart label device.

In another aspect, the method can further comprise transitioning, by the smart label control system, content for rendering on the display of the smart label device based on label criteria associated with the geo-locational boundary signal. In yet another aspect, the method can further comprise receiving, by the smart label control system, a set of manufacturing activity data from a manufacturing control system; triggering, by the smart label control system, a transmission of a subset of manufacturing activity data to the smart label device; and rendering, by the smart label control system, the subset of manufacturing activity data on a display of the smart label device.

In another method, the non-limiting computer-implemented method can comprise querying, by the server device, first location data acquired from the smart label device and stored on a database of the server device or a blockchain data store, wherein the first location data represents a current location of the smart label device; verifying, by the server device, that the first location data corresponds to second location data representing an authorized facility location, wherein the verifying is based on a comparison of the first location data to the second location data; and authenticating, by the server device, that user identification data received from a user device is authorized user identification data, wherein the authenticating is based on a comparison of the user identification data to the authorized user identification data.

The computer-implemented method can further comprise transmitting, by the server device, label update data to the smart label device based on a positive verification of the authorized facility and a positive authentication of the user identification data. Furthermore, the computer-implemented method can further comprise transmitting the first location data or the user identification data to a data store, wherein the data store is a blockchain data store or the database of the server device, wherein first location data recorded at the data store represents a chain of custody event, and wherein the user identification data recorded at the data store represents a chain of identity event.

What is claimed is:

1. A system comprising:
one or more processors; and
one or more storage devices comprising processor executable instructions that, responsive to execution by the one or more processors, cause the system to perform operations comprising:
receiving label identification data corresponding to a smart label device;
verifying whether the label identification data is valid or invalid;
assigning the label identification data to personal identification data representing a patient identifier,
curating a set of smart label data corresponding to a set of smart label devices;
applying one or more machine learning algorithms to the set of smart label data;
extracting insights from the set of smart label data based on the one or more machine learning algorithms;
tuning parameters of the one or more machine learning algorithms;
querying the set of curated smart label data for one or more insights; and
identifying one or more subsets of curated smart label data for a query analysis based on contextual parameters of a query, wherein the contextual parameters comprise at least one of a smart label device identifier, a geo-locational input, or authentication input.

2. The system of claim 1, wherein the operations further comprise receiving current coordinates corresponding to a current location of the smart label device.

3. The system of claim 2, wherein the operations further comprise:
comparing the current coordinates to boundary coordinates of an approved geo-locational boundary; and
determining whether the current coordinates are within the approved geo-locational boundary.

4. The system of claim 3, wherein the operations further comprise:
triggering a transmission of secure media content to the smart label device based on a verification that the current coordinates are within the approved geo-locational boundary, wherein the secure media content is at least one of textual content, audio content, or video content.

5. The system of claim 3, wherein the operations further comprise:
determining that the current coordinates are not within the approved geo-locational boundary;
removing secure media content from a display of the smart label device based on the determining that the current coordinates are not within the approved geo-locational boundary.

6. The system of claim 1, wherein the operations further comprise:
generating a set of manufacturing activity data from a manufacturing device;
triggering a transmission of a subset of manufacturing activity data to the smart label device; and
rendering the subset of manufacturing activity data on a display of the smart label device.

7. The system of claim 3, wherein the operations further comprise:
triggering a notification to a user device indicating the current location of the smart label device; and
prioritizing a biological material in a package queue for pickup or delivery based on the notification.

8. The system of claim 1, wherein the operations further comprise accessing a set of chain of custody event data or chain of identity data corresponding to the smart label device on a distributed ledger.

9. The system of claim 3, wherein the operations further comprise controlling the smart label device to render secure media content based on a set of label rules corresponding to a target facility associated with the approved geo-locational boundary.

10. A method, comprising:
receiving label identification data corresponding to a smart label device;
verifying whether the label identification data is valid or invalid;
assigning the label identification data to personal identification data representing a patient identifier,
curating a set of smart label data corresponding to a set of smart label devices;
applying one or more machine learning algorithms to the set of smart label data;
extracting insights from the set of smart label data based on the one or more machine learning algorithms;
tuning parameters of the one or more machine learning algorithms;
querying the set of curated smart label data for one or more insights; and
identifying one or more subsets of curated smart label data for a query analysis based on contextual parameters of a query, wherein the contextual parameters comprise at least one of a smart label device identifier, a geo-locational input, or authentication input.

11. The method of claim 10, further comprising:
receiving current coordinates corresponding to a current location of the smart label device.

12. The method of claim 11, further comprising:
comparing the current coordinates to boundary coordinates of an approved geo-locational boundary; and
determining whether the current coordinates are within the approved geo-locational boundary.

13. The method of claim 12, further comprising:
triggering a transmission of secure media content to the smart label device based on a verification that the current coordinates are within the approved geo-locational boundary, wherein the secure media content is at least one of textual content, audio content, or video content.

14. The method of claim 12, further comprising:
determining that the current coordinates are not within the approved geo-locational boundary;
removing secure media content from a display of the smart label device based on the determining that the current coordinates are not within the approved geo-locational boundary.

15. The method of claim 12, further comprising:
triggering a notification to a user device indicating the current location of the smart label device; and
prioritizing a biological material in a package queue for pickup or delivery based on the notification.

16. The method of claim 12, further comprising:
controlling the smart label device to render secure media content based on a set of label rules corresponding to a target facility associated with the approved geo-locational boundary.

17. The method of claim 10, further comprising:
generating a set of manufacturing activity data from a manufacturing device;
triggering a transmission of a subset of manufacturing activity data to the smart label device; and
rendering the subset of manufacturing activity data on a display of the smart label device.

18. The method of claim 10, further comprising:
accessing a set of chain of custody event data or chain of identity data corresponding to the smart label device on a distributed ledger.

* * * * *